US010010692B2

(12) United States Patent
Longest et al.

(10) Patent No.: US 10,010,692 B2
(45) Date of Patent: Jul. 3, 2018

(54) SYSTEMS, DEVICES, AND METHODS FOR CHANGING THERAPEUTIC AEROSOL SIZE AND IMPROVING EFFICIENCY OF VENTILATION AND AEROSOL DRUG DELIVERY

(71) Applicant: Virginia Commonwealth University, Richmond, VA (US)

(72) Inventors: Philip Worth Longest, Midlothian, VA (US); Michael Hindle, North Chesterfield, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 794 days.

(21) Appl. No.: 14/325,667

(22) Filed: Jul. 8, 2014

(65) Prior Publication Data
US 2015/0007817 A1    Jan. 8, 2015

Related U.S. Application Data

(60) Provisional application No. 61/843,681, filed on Jul. 8, 2013, provisional application No. 61/893,744, filed on Oct. 21, 2013.

(51) Int. Cl.
*A61M 16/10* (2006.01)
*A61M 16/14* (2006.01)
(Continued)

(52) U.S. Cl.
CPC .... *A61M 16/1085* (2014.02); *A61M 15/0086* (2013.01); *A61M 16/0833* (2014.02);
(Continued)

(58) Field of Classification Search
CPC .......... A61M 16/1085; A61M 16/0833; A61M 16/1095; A61M 15/0086; A61M 16/14;
(Continued)

(56) References Cited

U.S. PATENT DOCUMENTS 4,268,460 A * 5/1981 Boiarski ................ A61M 11/06
128/200.16
4,708,831 A * 11/1987 Elsworth ............. A61M 16/109
128/203.17
(Continued)

OTHER PUBLICATIONS

Longest et al. High-Efficiency Generation and Delivery of Aerosols Through Nasal Cannula During Noninvasive Ventilation. Journal of Aerosol Medicine and Pulmonary Drug Delivery. Oct. 2013;26(5):266-79. Mary Ann Liebert, Inc. Epub Dec. 28, 2012.
(Continued)

*Primary Examiner* — Todd J Scherbel
*Assistant Examiner* — Elliot S Ruddie
(74) *Attorney, Agent, or Firm* — W&C Intellectual Property

(57) ABSTRACT

A mixer-heater device provides controllable reduction in aerosol droplet size. Additionally, an intermittent delivery mode for administering an aerosol to a patient may take into account patient expiration and reduce aerosol losses without prolonging treatment time. Depositional losses in aerosol delivery systems may be reduced by streamlining the three dimensional geometry of conduits which change stream direction or flow path diameter. Ventilation systems may also benefit from streamlined components, in particular Y-connectors, with resulting advantages such as reduced rebreathed $CO_2$.

21 Claims, 17 Drawing Sheets

(51) Int. Cl.
| | |
|---|---|
| *A61M 16/08* | (2006.01) |
| *A61M 16/00* | (2006.01) |
| *A61M 15/00* | (2006.01) |
| *A61M 16/04* | (2006.01) |
| *A61M 16/06* | (2006.01) |
| *A61M 16/12* | (2006.01) |
| *A61M 16/16* | (2006.01) |

(52) U.S. Cl.
CPC ........ *A61M 16/1095* (2014.02); *A61M 16/14* (2013.01); *A61M 15/009* (2013.01); *A61M 16/0066* (2013.01); *A61M 16/0069* (2014.02); *A61M 16/04* (2013.01); *A61M 16/06* (2013.01); *A61M 16/0666* (2013.01); *A61M 16/12* (2013.01); *A61M 16/16* (2013.01); *A61M 2016/0024* (2013.01); *A61M 2202/064* (2013.01); *A61M 2205/3653* (2013.01)

(58) Field of Classification Search
CPC ............ A61M 16/0069; A61M 15/009; A61M 16/0066; A61M 16/04; A61M 16/06; A61M 16/0666; A61M 16/12; A61M 16/16; A61M 2016/0024; A61M 2202/064; A61M 2205/3653; A61M 11/001; A61M 11/02; A61M 11/06; A61M 15/00; A61M 15/0028; A61M 16/0841; A61M 16/109; A61M 16/142; A61M 16/164; A61M 2016/0039; A61M 2205/3368; A61M 2205/3606; A61K 31/235; A61K 31/4468; A61K 31/519; A61K 9/007; A61K 9/0073; B05B 17/04; B05B 7/1686; Y10S 261/48; Y10S 261/65
USPC ............ 128/200.14, 200.16, 200.21, 203.12, 128/203.15, 203.16, 203.17, 203.26, 128/203.27, 204.13, 204.25; 219/497; 239/338; 261/1, 104, 130, 142, 78.2, 261/DIG. 48, DIG. 65; 264/5; 424/45, 424/450, 46; 514/220, 54; 604/253
See application file for complete search history.

(56) References Cited

U.S. PATENT DOCUMENTS

| | | | |
|---|---|---|---|
| 4,911,157 | A | 3/1990 | Miller |
| 5,247,842 | A | 9/1993 | Kaufman et al. |
| 5,277,175 | A * | 1/1994 | Riggs ................. A61M 16/162 128/200.19 |
| 5,873,142 | A * | 2/1999 | Theiss ................... F22B 37/483 122/390 |
| 6,439,234 | B1 | 8/2002 | Curti et al. |
| 7,007,694 | B2 | 3/2006 | Aylsworth et al. |
| 7,267,121 | B2 | 9/2007 | Ivri |
| 7,802,569 | B2 | 9/2010 | Yeates et al. |
| 7,971,588 | B2 | 7/2011 | Fink et al. |
| 8,347,878 | B2 | 1/2013 | Schuschnig et al. |
| 8,651,105 | B2 | 2/2014 | Christopher et al. |
| 2003/0015197 | A1* | 1/2003 | Hale ...................... A61K 9/007 128/203.16 |
| 2004/0016427 | A1* | 1/2004 | Byron .................. A61M 11/041 128/200.14 |
| 2004/0047767 | A1* | 3/2004 | Bergman .......... B01L 3/502746 422/400 |
| 2008/0072899 | A1* | 3/2008 | Niland .................. A61M 16/14 128/203.16 |
| 2010/0252042 | A1* | 10/2010 | Kapust .............. A61M 16/0666 128/204.23 |

OTHER PUBLICATIONS

Longest et al. Improving Pharmaceutical Aerosol Delivery During Noninvasive Ventilation: Effects of Streamlined Components. Annals of Biomedical Engineering. Jun. 2013;41(6):1217-32. Biomedical Engineering Society. Epub Feb. 20, 2013.

Longest et al. Improving Aerosol Drug Delivery During Invasive Mechanical Ventilation with Redesigned Components. Respiratory Care. May 2014;59(5):686-98. The Journal Respiratory Care Company. Epub Oct. 8, 2013.

Dubus et al., "Aerosol Deposition in Neonata Ventilation", Pediatric Research, 2005, pp. 10-14 vol. 58, No. 1.

* cited by examiner

200

ADMIT AEROSOL DROPLETS AT AN INLET OF A MIXING REGION ~ 201

CONDUCT AEROSOL STREAM COMPRISING THE AEROSOL DROPLETS THROUGH CENTER CHANNEL ~ 203

HEAT AEROSOL STREAM WITHIN CENTER CHANNEL ~ 205

EMIT AEROSOL STREAM FROM CENTER CHANNEL ~ 207

┌─────────────────────────────────────────────┐
│   CONDUCT (HEATED) GAS STREAMS IN SIDE      │── 221
│              PASSAGES                        │
└─────────────────────────────────────────────┘
                      │
                      ▼
┌─────────────────────────────────────────────┐
│  ADMIT RECYCLED GAS FROM SIDE CHANNELS      │── 223
│            INTO MIXING REGION                │
└─────────────────────────────────────────────┘
                      │
                      ▼
┌─────────────────────────────────────────────┐
│   MIX RECYCLED GAS AND AEROSOL DROPLETS     │── 225
└─────────────────────────────────────────────┘
```

*FIG 2B*

```
                    ┌─────────────────────────────────────┐
                300 │                                     │
                 ↘  │ GENERATE A CONTINUOUS AEROSOL STREAM │──301
                    └─────────────────┬───────────────────┘
                                      ↓
                    ┌─────────────────────────────────────┐
                    │ PROVIDE A GAS STREAM SEPARATE FROM  │──303
                    │           AEROSOL STREAM            │
                    └─────────────────┬───────────────────┘
                                      ↓
                    ┌─────────────────────────────────────┐
                    │ COMBINE AEROSOL STREAM AND GAS STREAM│──305
                    │          TO FORM A MIXTURE          │
                    └─────────────────┬───────────────────┘
                                      ↓
                    ┌─────────────────────────────────────┐
                    │ DELIVER MIXTURE AS A THIRD STREAM TO│──307
                    │               PATIENT               │
                    └─────────────────┬───────────────────┘
                                      ↓
                    ┌─────────────────────────────────────┐
                    │ VARY FLOW RATE OF GAS STREAM WITH A │
                    │ FREQUENCY OF PATIENT RESPIRATION TO │──309
                    │ PROVIDE INTERMITTENT DELIVERY OF THE│
                    │             THIRD STREAM            │
                    └─────────────────────────────────────┘
```

*FIG 3*

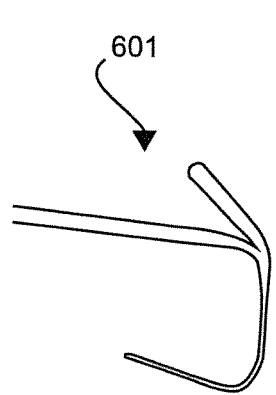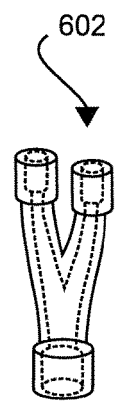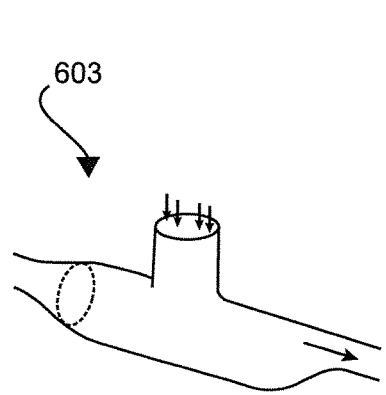
FIG 6A
FIG 6B
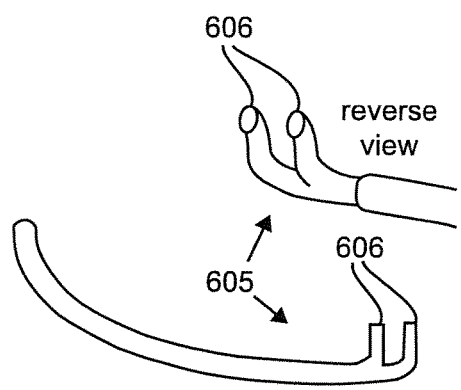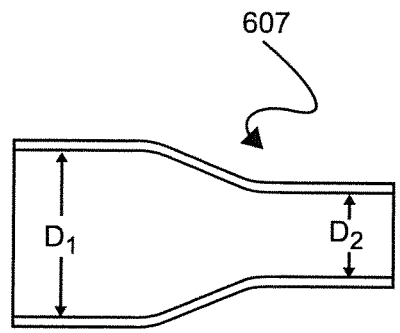
FIG 6C
FIG 6D

1000

```
┌─────────────────────────────────────┐
│  GENERATE A STREAM OF AEROSOL AND/OR │──1001
│              GAS                     │
└─────────────────────────────────────┘
                    │
                    ▼
┌─────────────────────────────────────┐
│  CONDUCT THE STREAM THROUGH ONE OR   │
│  MORE CONDUITS ALONG A PATH TO ONE OR│──1003
│  MORE PORTS DELIVERING THE STREAM TO │
│            THE PATIENT               │
└─────────────────────────────────────┘
                    │
                    ▼
┌─────────────────────────────────────┐
│  CHANGE A FLOW DIRECTION OF THE STREAM│
│  ALONG THE PATH, WHERE SUCH CHANGES   │──1005
│  ARE MADE WITH STREAMLINED CONDUIT    │
│            COMPONENTS                 │
└─────────────────────────────────────┘
```

(A) Base-10-T

Inlet from Aeroneb Lab nebulizer

Aerosol outlet 10 mm line (B) SLp-10-T

Inlet from Aeroneb Lab nebulizer

Perforated plate to unify the flow

Aerosol outlet 10 mm line (C) Base-10-CL

Reverse view

Inlet from T-connector 20 cm of 10 mm tubing 90° bend (D) SL-10-CL

Reverse view

Inlet from T-connector 20 cm of 10 mm tubing 90° bend

FIGS 14A-14D

SYSTEMS, DEVICES, AND METHODS FOR CHANGING THERAPEUTIC AEROSOL SIZE AND IMPROVING EFFICIENCY OF VENTILATION AND AEROSOL DRUG DELIVERY

CROSS-REFERENCE TO RELATED APPLICATIONS

This application claims priority of U.S. Provisional Patent Application No. 61/843,681 filed Jul. 8, 2013, and U.S. Provisional Patent Application No. 61/893,744 filed Oct. 21, 2013. The complete contents of both provisional applications are incorporated herein by reference.

STATEMENT OF GOVERNMENT INTEREST

This invention was made with government support under contract number R01 HL107333 awarded by the National Institutes of Health. The government has certain rights in the invention.

FIELD OF THE INVENTION

The invention generally relates to the treatment of respiratory disorders and, more particularly, devices and methods for aerosol drug delivery and ventilation.

BACKGROUND

The long-term practice of aerosol therapy during mechanical ventilation is continually evolving due to its unacceptable poor efficiency. This inefficiency partly results from the high losses of drugs in the ventilation components and the extrathoracic airways. The type of ventilator, mode of ventilation, type of patient interface, the aerosol generator and its configuration, aerosol particle size and breathing parameters have been identified as factors that influence the efficiency of aerosol therapy during ventilation.

High losses in the ventilation components and the extrathoracic airways could be avoided by optimizing the size of the aerosol to produce low aerosol losses and acceptable drug dose delivered to the lungs. Condensational growth of the submicrometer aerosols within the airways is one approach to prevent exhalation of the aerosol and is achieved either by the co-administration of supersaturated humidified air (enhanced condensational growth, ECG), as used in high flow therapy, or by addition of a hygroscopic excipient to the aerosol formulation, which enables growth using the natural humidity of the respiratory system (excipient enhanced growth, EEG). Studies of such techniques using steady inhalation flow conditions appeared to produce high emitted and lung doses, however the effects of realistic breathing profiles are known to create significant challenges for effective aerosol delivery during ventilation therapies. Thus, the benefit of condensational growth techniques during realistic breathing needs to be determined. A significant challenge is to overcome the losses of drug aerosol during exhalation. Pulsating aerosol delivery (aerosol delivered by pulsating aerosol generation) during the inhalation portion of the breathing cycle is one approach to minimize exhalation losses. Pulsating aerosol drug delivery has been used for numerous applications such as intermittent positive pressure breathing during ventilation and drug delivery to the sinuses. However, the effectiveness of this method has been controversial and not been apparent in all applications.

Mechanical ventilation is frequently used for cases of respiratory insufficiency that may arise from acute lung injury, acute respiratory distress syndrome, pulmonary disease, and cardiac failure. The two primary forms of mechanical ventilation are invasive and non-invasive. Both approaches are intended to deliver gases and frequently pharmaceutical aerosols to the lungs in a safe and efficient manner, with the goal of maintaining appropriate blood oxygen and carbon dioxide levels. Invasive mechanical ventilation may employ an endotracheal tube (ETT), tracheostomy tube, or laryngeal airway mask inserted to bypass the extrathoracic airways and provide access to the lungs. Non-invasive ventilation (NIV) delivers respiratory support with an interface at the nose and/or mouth. Common forms of non-invasive ventilation include low flow nasal cannula, non-invasive positive pressure ventilation with oral and/or nasal interfaces, and humidified high nasal flow cannula. Common problems related to mechanical ventilation include (1) $CO_2$ re-breathing of expired gas, (2) difficulty in weaning from invasive mechanical ventilation, (3) damage to the airways due to pressure and over inflation, especially for stiff and diseased lungs, and (4) poor delivery efficiency of pharmaceutical aerosols through the ventilator circuit. These issues are described in more detail below.

Mechanical ventilation seeks to supply oxygen and remove $CO_2$ from the blood. Both processes are necessary for successful mechanical ventilation. Too much $CO_2$ in the blood leads to hypercapnia, which is associated with tachypnea, dyspnea, reduced neural activity, raised blood pressure and eventually death. At $CO_2$ levels of approximately 3%, moderate respiratory stimulation to hypercapnia begins to occur. In mechanical ventilation systems there is an overlap region between the inspiratory and expiratory lines. Within this overlap region, also termed ventilator dead space, a portion of the expired breath is held and then re-breathed on the next inhalation. This re-breathing can increase the $CO_2$ concentration of the inspired air potentially leading to hypercapnia. Moreover, mixing of the expired air with the air in the inspiratory line can increased the re-breathing of $CO_2$. Current methods to prevent re-breathing $CO_2$ include implementing a bias flow on the system to flush out $CO_2$ [4] and the use of dual lumen ETTs. However, bias flow may result in elevated ventilation flow rates, which may be injurious to the airways. Dual lumen ETTs complicate the system and would be difficult to apply to the very narrow airway passages of neonates.

Weaning from invasive mechanical ventilation is a very difficult process that frequently fails, requiring re-administration of ventilation support. The readiness for weaning from the ventilator is typically assessed by the evaluation of spontaneous breathing effectiveness over a period of 30 to 120 minutes, often while still connected to the ventilator. Spontaneous breathing is also encouraged by most ventilator systems in order to maintain the muscle tone and ventilatory drive of the patient. As a result, the mechanical ventilation system should make spontaneous breathing as easy as possible. However, high flow resistance of the ventilatory circuit provides an additional hurdle to spontaneous breathing. The resistance in the ventilatory circuit and its effect on spontaneous ventilation have not been previously considered.

Mechanical ventilation may cause damage to the airways by over-pressurizing or over-inflating the alveolar airspace (barotrauma and volutrauma). This can lead to airway inflammation, increased lung resistance, decreased compliance, and difficulty with continued ventilation. Frequent opening of collapsed alveoli can also lead to inflammation.

Positive end-expiratory pressure (PEEP) is typically set to maintain open alveolar airspace throughout the breathing cycle. The cyclic pressure and volume peak values superimposed on PEEP can induce barotrauma and volutrauma. Ideally, the required volume flow should be delivered to the lungs with a minimum peak pressure value above the PEEP setting. To control peak pressures, current ventilators have a pressure-based delivery mode and/or limits in place to avoid pressures above a maximum value. For high resistance systems, limiting the pressure also limits the flow rate that can be achieved. Lung injury can be reduced by delivering a desired amount of gas flow (volume) with a minimum pressure rise above the PEEP setting. This is especially important in cases of diseased and/or inflamed lungs where compliance is reduced and resistance is increased.

For conventional aerosol drug therapy during NIV, drug delivery efficiencies through the ventilation circuit are typically <1-10% in adults and children based on in vitro experiments and 1-6% in vivo evidence. Differences between in vitro and in vivo estimates are often due to the absence of humidified conditions and the absence of an exhaled fraction in the in vitro experiments. Previous studies of aerosol delivery efficiency with nasal cannula interfaces have focused on low flow rates in adult and infant models. Bhashyam et al. considered aerosol delivery from a mesh nebulizer (Aeroneb Solo, Aerogen Limited, Galway, Ireland) through infant, pediatric, and adult nasal cannulas at an inspiratory flow rate of 3 liters per minute (LPM) with a heated and humidified system. Drug depositional losses in the connectors, tubing, and cannula resulted in a total output that ranged from 19-27% of the initial dose when simulated inhalation was included in the system. Ari et al. considered aerosol delivery from the Aeroneb Solo device through an Optiflow (Fisher and Paykel, Irvine, Calif.) pediatric nasal cannula at flow rates of 3 and 6 LPM with oxygen or heliox. The maximum cannula aerosol drug delivery efficiency of approximately 10% occurred with a flow rate of 3 LPM and was decreased significantly with the use of the higher flow rate and heliox.

Respiratory drug delivery during mechanical ventilation with an endotracheal tube (invasive mechanical ventilation) is known to be inefficient based on in vitro and in vivo studies. Lung drug delivery efficiency values for pressurized metered dose inhalers and nebulizers administered during ventilation are typically less than 10% during all forms of mechanical ventilation. Vibrating mesh nebulizers have increased aerosol delivery efficiencies to values in the range of 10-25% based on in vitro studies of invasive ventilation. Inhalation triggering of a vibrating mesh nebulizer coupled with aerosol delivery during a portion of the inspiration flow further increased delivery efficiency to values as high as 60%. However, one disadvantage of breath activated mesh nebulizers is the relative cost and complexity of the system compared with other aerosol delivery technologies.

Previous studies have observed high aerosol drug losses during mechanical ventilation in the aerosol source adapter, connectors, and endotracheal tube (ETT). Based on these high depositional losses, it can be concluded that current commercial ventilator circuits are not designed for the efficient delivery of aerosols. A practical and cost effective method to improve aerosol delivery efficiency during mechanical ventilation is to redesign the ventilator circuit components responsible for high aerosol deposition losses in ways that also have a positive effect on gas delivery. In U.S. Pat. No. 7,290,541, Ivri et al. suggest that low angles at ventilator circuit transition points (<15°) can be used to improve aerosol delivery during mechanical ventilation. However, these low angles typically require additional lengths of ventilator tubing and/or line positioning which may not be practical in critical care settings. Increasing the tubing length will also increase aerosol loss by sedimentation and may increase ventilator dead space and $CO_2$ re-breathing. In most practical aerosol delivery systems, the aerosol stream is required to change direction by an angle of 90° or more and the conduit size changes diameter at least once. In some systems, multiple changes in direction and conduit size are required. For example, an invasive mechanical ventilation system may include a T-connector, Y-connector, and endotracheal tube that curves through the extrathoracic airways. As the aerosol moves through the Y-connector, there is a minimum 90° change in direction followed by an approximately 90° change in direction in the endotracheal tube. As a result, the aerosol stream has changed direction by 180°, not including additional changes in direction in the connective tubing as well as changes in conduit size.

SUMMARY

Mixer-heater devices are provided which, in exemplary embodiments, improve respiratory aerosol delivery. Exemplary mixer-heaters reduce aerosol size while minimizing depositional drug losses. Reducing aerosol size is desirable for techniques such as excipient enhanced growth (EEG) and enhanced condensational growth (ECG).

An intermittent mode of aerosol delivery maximizes the aerosol drug dose delivered to the lungs and minimizes exhalation losses, especially as compared to a continuous mode commonly employed in the art. Current use of intermittent delivery cycles the nebulizer on and off consistent with respiration. In contrast, an approach described herein allows for continuous nebulization into a mixer or reservoir with low depositional loss and cycles delivery airflow to provide intermittent delivery consistent with respiration. Using this approach, the aerosol delivery rate can be doubled compared with cycling the nebulizer on and off.

During invasive mechanical ventilation, streamlined components and in particular a streamlined Y-connector may reduce $CO_2$ re-breathing. With conventional Y (i.e. "wye") geometries, flow disruption in the Y-connector during exhalation may cause mixing of the expired gas into the inspiratory lines. As a result, an increased fraction of $CO_2$ is re-breathed. Similarly during inhalation, mixing in the Y region can pull high concentration $CO_2$ gas from the expiratory line into the inspiratory gas stream. Properly designed streamlined geometries according to the teachings herein can reduce this mixing of $CO_2$ into the inspiratory flow and decrease the amount of $CO_2$ rebreathed into the lungs. Ideally, the concentration of $CO_2$ exiting the endotracheal tube (ETT) and entering the lungs should be as low as possible and at least below 3% $CO_2$.

In some exemplary embodiments, streamlined components significantly reduce pressure drop and resistance to flow through the mechanical ventilation system. For invasive mechanical ventilation, a streamlined Y-component may make spontaneous or unassisted breathing easier when the ventilation circuit is in place. This allows the patient to spontaneously breath more effectively both during ventilation administration and during weaning.

For invasive mechanical ventilation, a majority of pressure loss typically occurs in the Y-connector. As a result, a streamlined Y-connector can effectively reduce the peak magnitude of the input pressure waveform required to drive a specific inhaled volume. By reducing the pressure wave magnitude, reduced barotrauma is expected in the lung. This approach does not alter the PEEP pressure level, which is constant and used to maintain open alveoli.

During pharmaceutical aerosol drug delivery with invasive mechanical ventilation, a majority of the aerosol is usually lost in the Y-connector. Redesigning the Y-connector with a streamlined three dimensional geometry may reduce unwanted aerosol drug loss and significantly improve aerosol drug delivery to the lungs.

Aerosol drug delivery during noninvasive ventilation has a number of advantages. For example, aerosol drug delivery with high flow nasal cannula therapy allows the patient to continue receiving ventilatory support while the aerosol is administered. A majority of aerosol loss with NIV occurs in the connector associated with the aerosol generation device and in the patient interface (e.g. nasal cannula). By redesigning these components with a streamlined three dimensional geometry, aerosol delivery to the lungs may be significantly improved.

Applications of the invention may include, but are not limited to, the following:
- Drug delivery during mechanical ventilation—both invasive and non-invasive.
- Respiratory drug delivery to infants and children where current state-of-the-art devices only provide approximately 1% of the initial dose to the lungs.
- Effective lung delivery for aerosol testing in animals.
- Submicrometer generation sources for controlled condensational growth technology (EEG and ECG).
- Delivery of inhaled medications with short durations of action over long time periods with nasal interfaces.
- Addition of medical aerosols to non-invasive ventilation systems without interrupting ventilation therapy.
- Practical and efficient delivery of aerosol through the nose to the lungs.
- Improving treatment of nasal conditions with respiratory aerosols, such as chronic and acute sinusitis and infections that can be transferred to the lungs.
- Nose-to-brain delivery of drugs.

BRIEF DESCRIPTION OF THE DRAWINGS

FIGS. 2A and 2B are methods for reducing aerosol droplet size;

FIG. 3 is a method for aerosol administration using intermittent delivery;

FIGS. 6A-6D are exemplary streamlined conduit components;

FIG. 10 is a method for delivering a gas or aerosol with a streamlined approach;

FIG. 11 shows intermittent (A) 2-second and (B) 1-second aerosol delivery during simulation of the breathing profile 1;

FIG. 14 shows individual components of the noninvasive delivery system for an adult including the (A) commercial Aerogen Neonatal T-connector (Base-10-T), (B) streamlined mesh nebulizer T-connector (SLp-10-T), (C) commercial Optiflow nasal cannula, medium size (Base-10-CL), and (D) streamlined nasal cannula (SL-10-CL)

DETAILED DESCRIPTION

Figure 1A:
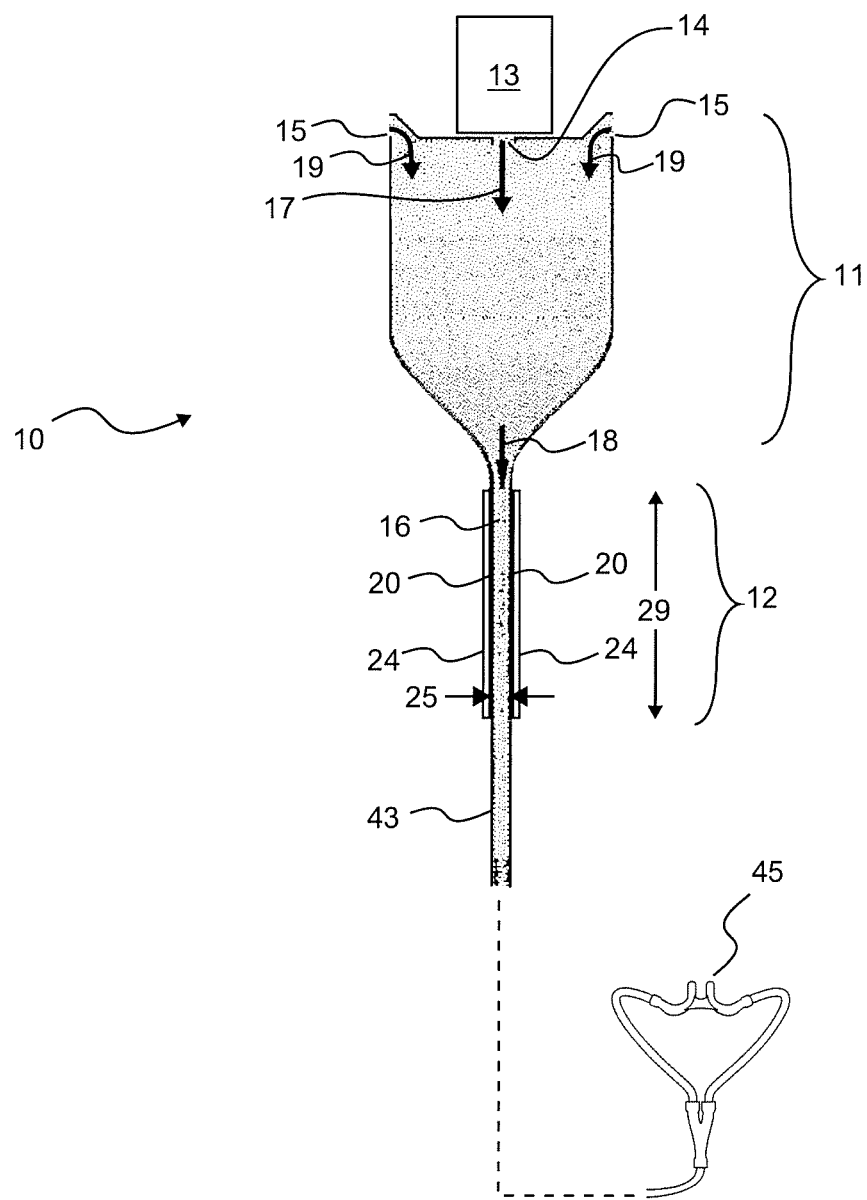
FIGS. 1A-1D are mixer-heater devices for reducing aerosol droplet size.

Though features of the invention may be described and illustrated herein with respect to particular exemplary embodiments, it should be understood that features are not limited to the exemplary embodiments shown and discussed, and that features of one exemplary embodiment may be combined with compatible features of other exemplary embodiments in the practice of the invention. The embodiments shown and described are illustrative only. Where features correspond between exemplary embodiments, the same reference numerals may be used in their respective figures.

Referring now to the figures, and more particularly FIG. 1A, a general mixer-heater device 10 has the functionality of reducing aerosol droplet size. This may be desirable, for example, when a particle or droplet size of an aerosolized medicament/drug is needed for a particular respiratory drug delivery method or technique. Aerosol size may be measured by, for example, mass median aerodynamic diameter (MMAD). Many commercial nebulizers produce particles (typically droplets) which are too large for drug delivery techniques such as, for example, enhanced excipient growth (EEG) and enhanced condensational growth (ECG). In such applications, a mixer-heater 10 may be used to give precise, controlled, and adjustable particle size reduction. One advantage of a stand-alone mixer-heater 10 is compatibility with virtually any existing nebulizer 13 (shown schematically in FIG. 1A). In an exemplary aerosol delivery system, the mixer-heater 10 need only be arranged to receive the aerosol generated by the nebulizer 13. In alternative embodiments, a mixer-heater 10 may be integral with a nebulizer.

At a general level, a mixer-heater 10 comprises at least a mixing region 11 and a channel portion 12. In some exemplary embodiments, the mixer-heater device 10 is arranged vertically, with mixing region 11 above channel portion 12. The two elements are typically formed integrally with one another, distinctive in their differing cross-sectional sizes and functions. As shown in FIG. 1A, an exemplary mixer-heater 10 may have a polygonal cross-section (not shown), or, more particularly, a rectangular cross section. Although alternative cross-sectional shapes may also be employed in alternative embodiments, a configuration with a rectangular cross-section for the channel portion 12 has been found preferable as compared to a configuration with a rounded cross-section for channel portion 12.

The basic operation of a mixer-heater 10 will be explained in reference to FIG. 2A showing a method 200 for reducing aerosol droplet size. At step 201, aerosol droplets are admitted to a mixing region 11 at an inlet 14 of a mixer-heater 10. This is indicated by arrow 17 in FIG. 1A. The device which generates the aerosol, typically a nebulizer 13, may be arranged at the inlet 14 or connected to the inlet by one or more intervening conduits which conduct the initial aerosol stream from the nebulizer 13 to the inlet 14. Once admitted to the mixing region 11, aerosol droplets may interact with one or more gases which are already present in the mixing region 11 and/or which are admitted to the region separately as one or more gas streams. In embodiments which admit separate gas streams, these are generally admitted at inlets 15 at a top portion of the mixing region 11. The admission of separate gas streams is indicated in FIG. 1A by arrows 19. As its name suggests, mixing region 11 is configured to permit or facilitate the mixing of the aerosol droplets and gases. At this stage, the droplets may begin to evaporate. The droplets comprise at a minimum some liquid, frequently but not necessarily always a solvent or carrier for a medicament or drug also within the droplets. A mixer-heater 10 reduces droplet size by evaporating a controlled amount of the liquid content of the droplets. Evaporation converts some of the solvent or carrier from a liquid to a gas.

In one exemplary embodiment, used in Example 1, the mixing region (i.e. mixing chamber) had cross-sectional dimensions in a direction perpendicular to flow of 12 cm×14 cm with a total volume 1.8 L in this rectangular region. Sigmoidal curves were used to connect the rectangular mixing chamber to the channel portion over a distance of 16 cm, which introduced an additional volume. In a 2nd exemplary embodiment, used in Example 2, the mixing chamber had cross-sectional dimensions in a direction perpendicular to flow of 8 cm×8 cm with a total volume 0.64 L in this rectangular region. Sigmoidal curves were used to connect the rectangular mixing chamber to the channel portion over a distance of 8 cm, which introduced an additional volume. As illustrated in the Examples, both designs performed well with low aerosol losses in the mixer even with intermittent aerosol delivery. The mixer is preferably designed such that that its volume and geometry accommodate the incoming aerosol and air while achieving low depositional losses of the aerosol. This is in contrast to using ventilation tubing and a commercial T-connector to accommodate the mixing, which produces high depositional losses (Example 7; CM-Wye).

After the aerosol droplets have passed through the mixing region 11, a stream comprising the aerosol droplets is conducted through a center channel 16 of the channel portion 12 (step 203 of FIG. 2A). This stream and its flow direction is indicated in FIG. 1A by arrow 18. The individual droplets themselves within the stream may individually exhibit some non-linear movement, but the net movement of the droplets and therefore the stream is in the direction indicated by arrow 18. If the mixer-heater 10 is arranged vertically as previously discussed and shown in FIG. 1A, the direction of flow is in the direction of Earth's gravitational pull.

Figure 1B:
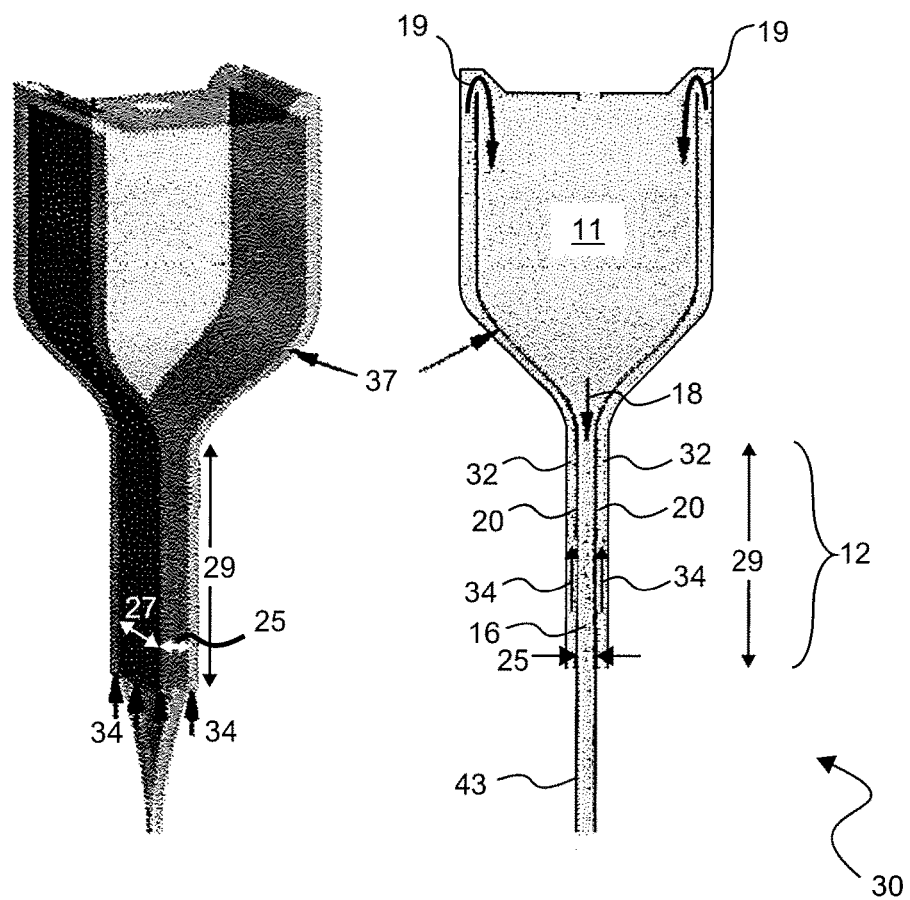

The center channel 16 includes opposing walls 20 which, in exemplary embodiments, form a pair of opposing walls which may be planar and run the length of the center channel 16. This contributes to the characteristic rectangular cross-section of the channel portion 12 previously discussed. The center channel 16 is relatively narrow, with one exemplary cross-sectional profile of 1.2 cm wide and 8 cm deep. The channel width 25 (narrowest part of the cross-section) could range from approximately 0.5-3.0 cm. A rectangular shape is implemented with the width 25 having a smaller dimension than the depth 27 (e.g. as shown in FIG. 1B). This configuration was found to maximize heat transfer and aerosol evaporation while minimizing aerosol depositional loss and required channel length 29 in the direction of aerosol transport. The depth 27 is typically proportional to the width 25 with a characteristic ratio of depth to width of 8 cm/1.2 cm=6.7. Other depth to width ratios could be implemented to maximize heat transfer and minimize aerosol loss depending on the desired flow rate with a depth to width ratio typically greater than or equal to 1.5, or more advantageously greater than or equal to 2.0, 3.0, 4.0, 5.0, 6.0, etc. The depth may range from approximately 0.75 cm to 30.0 cm. Length 29 of the flow passage in the direction of flow in one exemplary embodiment is 15 cm, but may be adjusted to ensure the desired evaporation of the aerosol occurs depending on the implemented flow rate. As the aerosol stream is conducted through the center channel 16 of the channel portion 12 (step 203 of FIG. 2A), the two opposing planar walls 20 heat the passing droplets (step 205). In some preferred embodiments, the aerosol stream is heated to 28-70° C. Even more preferably, the aerosol stream is heated to 30-42° C. This temperature is generally the aerosol stream temperature as it is emitted from the center channel 16 (step 207). The desired temperature is selected based on an acceptable temperature for the patient to inhale comfortably while producing the required aerosol particle size. Higher temperatures (i.e., >42° C.) may be desirable for using the device to produce dry powders of medication for collection and subsequent use in, for example, a dry powder inhaler. In addition to heating the stream emitted from center channel 16, mixer-heater 10 may also desirably increase the relative humidity (RH) of the emitted stream to ensure patient comfort during the delivery period. The relative humidity of the emitted stream may be elevated by increasing the relative humidity of the gas streams which are mixed with the aerosol stream. Evaporation of water from the nebulizer aerosol droplets may also contribute to the increase in RH.

Heating of an aerosol stream within center channel 16 via the opposing walls 20 may be accomplished in different ways. According to some exemplary embodiments, heating elements 24 (e.g. resistive heating elements such as a resistive film) are arranged on or integral with the walls 20. The current, voltage, or power supplied to these heating elements 24 may be carefully controlled to set, adjust, or otherwise regulate the temperature profile within the center channel 16.

By using two walls of the narrow rectangular channel for heating, the length of the heating channel is minimized, providing a more compact device, which is typically desirable. To maximize heat transfer, the two widest opposing walls of the rectangular channel geometry are preferably heated. In an alternative configuration, one wall may be used for heating the flow stream; however, this would increase the required channel length to achieve a set amount of heating thereby increasing the device size unnecessarily.

According to still other exemplary embodiments, heating of an aerosol stream within channel 16 may be accomplished by counter current heat exchange across the opposing walls 20. Mixer-heater 30 shown in FIG. 1B is one such exemplary embodiment. In addition to a mixing region 11 and channel portion 12, mixer-heater 30 additionally comprises one or more side channels 32 (typically two) separated from the center channel 16 by the opposing walls 20. The side channels 32 are configured to conduct gas streams in a direction 34 which is opposite the direction 18 of the stream within the center channel 16. The gas streams in the side channels 32 are made to be a temperature which is generally greater than or equal to a temperature of the aerosol stream at the point where the aerosol stream enters the center channel 16 (e.g. at the top of the center channel 16 according to the configuration shown in FIG. 1A). FIG. 2B shows a method 220 for providing counter current heat exchange in a mixer-heater 30. In practice, method 200 and method 220 may occur together with steps from each method being conducted concurrently. It should be additionally noted that the individual steps of both methods 200 and 220 are shown in a sequence for illustrative purposes only, and some or all steps may occur in an order different from that which is shown and, in particular, at the same time during continuous operation of a mixer-heater 10 or 30.

In FIG. 2B, conducting heated gas streams in side channels 32 adjacent to center channel 16 is indicated by step 221. To permit the counter current heat exchange, opposing walls 20 of mixer-heater 30 are configured to be heat conductive (e.g. by comprising a heat conductive material such as metal). Since the gas streams in side channels 32 are warmer/hotter than the aerosol stream in the center channel 16 at any longitudinal point along the channels, walls 20 are cooler than the gas streams at a given longitudinal point. Heat from the gas streams is absorbed by the walls 20, and the walls 20 then emit this energy as thermal radiation into the center channel 16, heating the aerosol stream. The heating of the aerosol stream results in partial evaporation of the droplets, reducing their size. In some embodiments, one or more of the gas streams in side channels 32 may be admitted as recycled gas to the mixing region 11 of the mixer-heater 30 (step 223 of FIG. 2B). The recycled gas is then mixed with aerosol droplets (step 225) which have not yet been conducted as a stream through the channel portion 12.

In some embodiments, the heating elements 24 shown in FIG. 1A and the side channels 32 shown in FIG. 1B may be used together in the same mixer-heater. In this case, the heating elements 24 may be used to heat both the aerosol stream within the center channel 16 and the gas streams in side channels 32. Heating elements 24 may be arranged on just one side of walls 24 to preferentially heat the aerosol stream or, alternatively, the gas streams. In an alternative embodiment, separate heating elements 24 may be arranged on either side of walls 24 or within the walls. Countercurrent heat exchange may be included, if the walls 24 are conductive. In some embodiments, the walls 24 may be insulated such that thermal energy in the gas streams in the side channels 32 does not transfer to the center channel 16 via walls 24. Instead, the heated gas streams transfer thermal energy to the aerosol droplets in the mixing region when the gas streams are recycled according to steps 223 and 225 of method 220 (FIG. 2B). Generally, insulated walls 37 may be provided between the side channels 32 and the interior of mixing region 11 to limit heat transfer between gas streams and aerosol droplets to either or both the channel portion 12 (in the case of counter current heat exchange) and the interior of the mixing region 11 (in the case of recycling the gas streams for mixing).

Figures 1C, 1D:
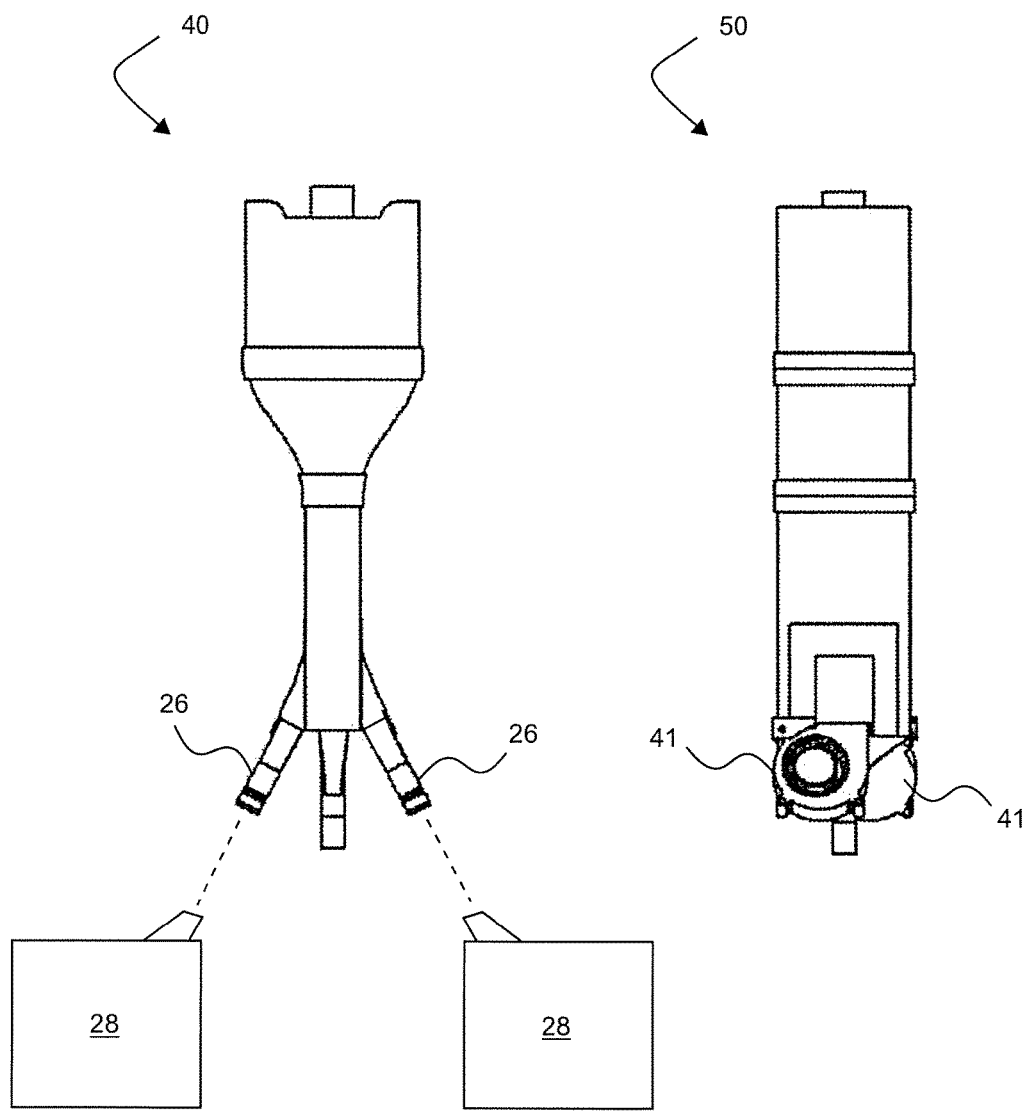

FIGS. 1C and 1D shows two mixer-heaters 40 and 50 with exemplary inlet arrangements for supplying gas streams to side channels 32. In FIG. 1C, inlet ports 26 are arranged at a start of side channels 32. These inlet ports 26 permit a connection with one or more external pressurized gas sources 28 (shown schematically in FIG. 1C). Heating of the gas streams may be performed and regulated by the external pressurized gas sources 28 such that the gas streams are of a desired temperature upon entering the side channels 32. Alternatively, heating of the gas streams may be performed according to the methods described above in connection with FIGS. 1A and 1B. FIG. 1D shows an exemplary mixer-heater which has one or more fans 41 instead of inlet ports 26. This configuration has the advantage that no external pressurized gas sources 28 are required to generate the flow of gas streams in side channels 32. In either case, volumetric flow rate of the gas streams in the side channels 32 may be regulated and controlled to be of a particular value or fall within a particular control range. The flow rate of the gas streams may also be varied over time. If the gas streams are recycled into the mixing region 11 of the mixer-heater, control of the gas stream flow rate (by, for example, either by external pressurized gas sources 28 or fans 41) may be used to provide or facilitate control over the volumetric flow rate of the aerosol stream passing through and emitted from the center channel 16. According to some exemplary embodiments, the aerosol stream in the center channel 16 is emitted from the center channel 16 at a flow rate of 1 to 60 L/min. Flow rate of the emitted stream is preferably selected and set according to the particular application for which the heater-mixer is being used. As an example, for continuous ventilation support during high flow therapy (HFT) in adults, the effective operating range of the device may be 10 to 15 L/min. Flow rate ranges between 1.0-60 L/min may be employed during other forms of non-invasive ventilation and during invasive mechanical ventilation. For example, flow rates of 10-60 LPM may be used during high flow nasal cannula therapy in adults. A flow rate of 2-20 LPM may be used in high flow nasal cannula therapy in children. A flow rate of 1-5 LPM may be used in low flow nasal cannula oxygen support in adults and children. Typically, the emitted stream is admitted to one or more conduits 43 (e.g. cannulas, endotracheal tube, or face mask) which conduct the stream to one or more ports 45 which deliver the aerosol droplets to a patient. The cannula application is shown schematically in FIG. 1A.

Generally, the aerosol stream emitted from the center channel 16 has droplets which, due to the evaporation performed by the mixer-heater, have been reduced from a size larger than 2 μm, for example, to a size smaller than 2 μm, for example. In an exemplary embodiment, aerosol droplets are reduced to submicrometer size (i.e. size is less than or equal to 1 μm). As previously indicated, the droplet size may be selected and the mixer-heater configured for such selection based on the application or treatment (e.g. EEG or ECG).

An advantage of mixer-heaters according to the teachings herein is reduced depositional losses of an aerosol delivery system used to administer an aerosol (frequently an aerosolized medicament) to a patient. Techniques such as EEG and ECG increase the total dose delivered to the patient, and mixer-heaters such as those shown in FIGS. 1A-1D provide aerosol streams which are suited for these techniques. Generally, smaller aerosol droplets have lower depositional losses, both in delivery system components such as cannulas as well as within the extrathoracic airways of a patient's respiratory tract. EEG and ECG advantageously transport small droplets to target deposition sites and, only when nearing or at such sites, increase droplet size to encourage deposition.

High depositional losses also occur for reasons other than large aerosol droplet size in conduits and non-target sites of the human respiratory tract. One particular source of loss is patient expiration. In order for an aerosol to pass from an aerosol delivery system to a patient's airways, some airflow must exist into the patient's airways. Generally, this corresponds with the direction of flow during human inspiration (e.g. as a patient breathes in). During expiration, however, there is a net volumetric flow of gas and air out of the patient and new aerosol droplets which are not already inside the patient airways are prohibited from entering the respiratory tract until the subsequent inspiration. Human respiration is cyclical, with inspiration and expiration each representing approximately half of the total time of each cycle.

In more rudimentary aerosol delivery systems, the respiratory cycle of a patient is ignored entirely. Such a system may operate in a "continuous delivery mode", meaning the nebulizer remains on and continues to generate an aerosol during both inspiration and expiration. A problem with this technique is that an aerosol stream containing the drug aerosol may be emitted by the system, but this stream cannot be delivered to the patient during exhalation, and the droplets may be forced to deposit in conduits or driven into the ambient air upon exit from a delivery port in the direction of the patient but diverted by the patient's exhaled breath. The aerosol stream within the conduit may even be inverted by the patient's exhaled air, driving the droplets back toward the nebulizer or through an outlet intended to disperse such a reverse in conduit flow. In either case, undesirable aerosol losses result.

Aerosol delivery systems which take into account patient expiration commonly operate in what may be referred to as a "pulsating aerosol delivery mode", meaning the cyclic respiratory cycle of a patient is used to trigger the nebulizer on and off with each individual respiratory cycle. Sensors may be arranged to detect a change such as the flow rate in a patient's airway and, when the change in flow rate is indicative of the expiratory phase of a respiratory cycle, the nebulizer is temporarily switched off so no new aerosol droplets are generated. The nebulizer is then switched back on when the patient begins the inspiratory phase of the respiratory cycle. Although the approach of a "pulsating aerosol delivery mode" eliminates aerosol generation when the droplets cannot be administered to the patient, it has multiple disadvantages. Although the nebulizer is shut off, aerosol may still be present in the conduits arranged between the nebulizer and patient. Without a pressure gradient driving the aerosol toward the patient, the aerosol may instead deposit in the conduits. Furthermore, the time required to deliver a particular drug dose is essentially doubled. Theoretically, if a given dose of aerosolized medicament is normally administered by a continuously operating nebulizer over a continuous time interval "t", but now the nebulizer is shut off for half of each individual respiratory cycle, then the total continuous time interval required to nebulize the same given dose according to the "pulsating aerosol delivery mode" is "2t", or twice the time in "continuous delivery mode". In addition, the nebulizers are traditionally designed to operate in constant delivery mode; the effects of repeatedly cycling the nebulizer on and off on the aerosolization efficiency is unknown.

Referring now to FIG. 3, a method 300 is provided for administering an aerosol to a patient with minimized depositional losses and improved efficiency over known techniques. Method 300 exemplifies a technique which may be referred to as "intermittent aerosol delivery mode". According to this approach, an aerosol flow is not wastefully emitted from the system while a patient is expiring. However, the aerosol generating device may remain on and continue to generate a continuous and constant stream, thereby eliminating the need to increase or double the total time over which the aerosol is administered to a patient to achieve the desired total dose.

At step 301, a continuous aerosol stream is generated with an aerosol generating device (for example, a nebulizer). This stream may be continuous, meaning there is no pause in the generation of new aerosol droplets, as well as constant, meaning the number of new droplets generated per unit time remains substantially the same. If desired, the continuous aerosol stream may be non-constant, with the number of new droplets per unit time varying over time (so long as the number is greater than zero). Separate and apart from the aerosol stream, at least one gas stream is provided by a pressurizing device (step 303). The continuous aerosol stream and the gas stream are then combined in a mixing reservoir, forming a mixture (step 305). This mixture is delivered as a third stream to a patient (step 307). Whereas the aerosol stream generated by the nebulizer is continuous, the gas stream and the mixture stream are variable and non-continuous. As indicated at step 309, a flow rate of the gas stream may be varied with a frequency of patient respiration such that the flow rate can be synchronized with a patient's individual respiration frequency. Synchronizing reductions of the gas stream flow rate with patient expiration provides periodic temporary retention of the mixture in the mixing reservoir and intermittency to the delivery of the mixture stream to the patient.

An important feature contributing to the improved effectiveness of method 300 as compared to known aerosol delivery techniques is that flow out of the system (i.e. the mixture stream) is regulated indirectly via control of the independent gas stream. In contrast, existing systems either have continuous flow out of the system or change the system output by turning on and off the aerosol stream generated by the nebulizer. Furthermore, the provision of a mixing reservoir allows for retention and accumulation of new aerosol droplets which are generated while a patient is expiring. Thus, during subsequent inspiration, the patient may inhale a greater quantity of aerosol.

An exemplary range of frequencies by which the flow rate of the gas stream may be varied is 12-50 cycles per minute. This range would be applicable to, for example, both human neonates and an exercising human adult. Alternatively, the frequency may be, for example, 6-7.5 cycles per minute. This range would be more suitable for guided deep inspiration, where a single inspiration may take 8-10 seconds. Although an intermittent delivery mode method such as method 300 is particularly well suited for administering an aerosol to a human patient, animal patients are likewise contemplated. That is to say, "patient" as used herein may be a human or animal, such as but not limited to horses and dogs or laboratory test animals. In veterinary applications, the flow rate of the gas stream should be varied with a frequency of respiration corresponding with the particular animal species in question.

Reductions in flow rate may be as low as terminating flow rate (i.e. zero flow rate). Synchronization of reductions in flow rate of the gas stream with patient expiration may be accomplished in different ways. One exemplary approach may be to set the frequency of a pressurizing device generating the gas stream and to then instruct a patient to synchronize his or her breathing with the device. This may be facilitated with, for example, indicators such as a light which turns on when the patient should inhale and off when the patient should exhale. Alternatively, one or more sensors may be used to detect the respiration frequency of a patient and/or identify expiration by the patient. The timing and frequency of gas stream flow rate reductions may then be based on the detected frequency and expiration timing.

Figure 4:
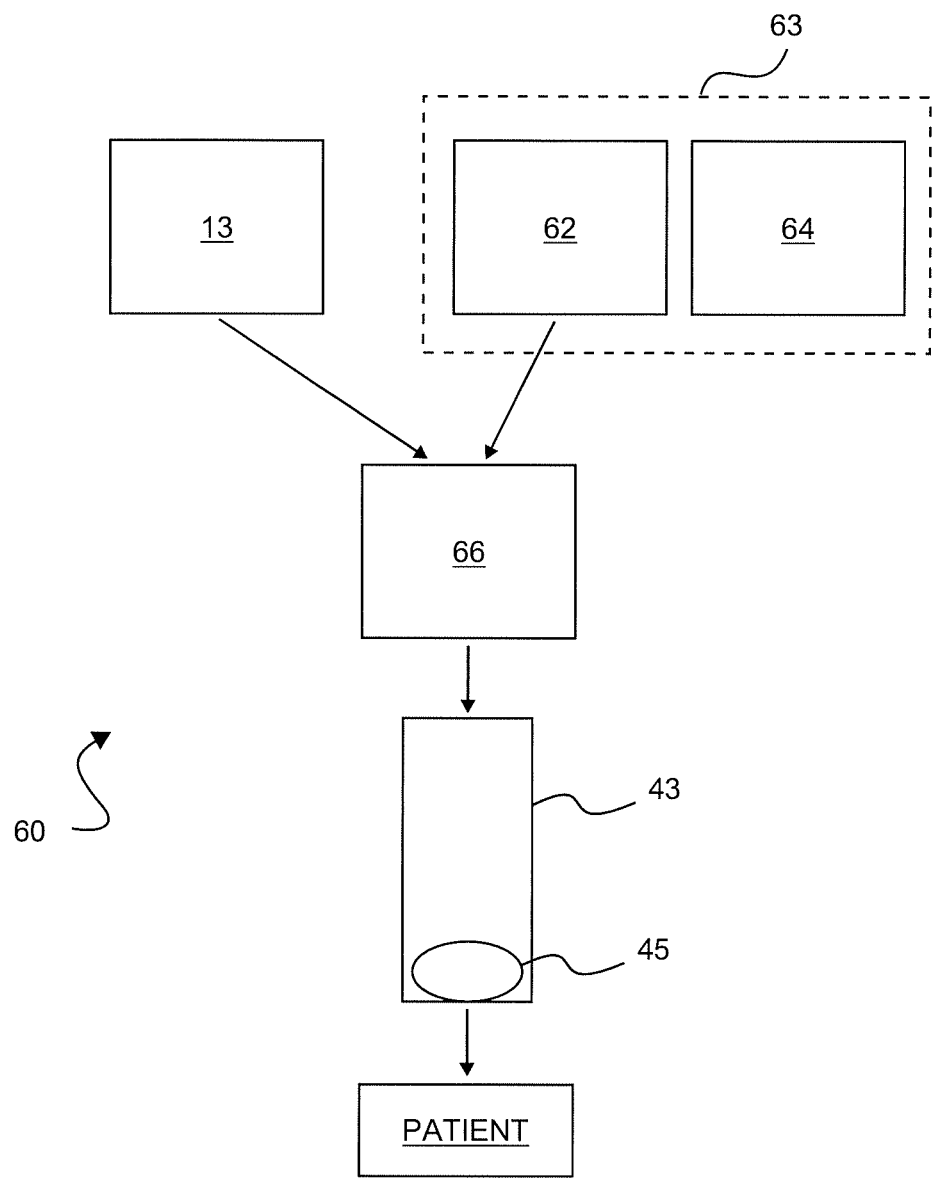
FIG. 4 is a block diagram for a system for intermittent aerosol delivery.

FIG. 4 schematically shows a system 60 for performing aerosol administration to a patient according to a method of intermittent delivery mode, for example method 300 of FIG.

3. Aerosol delivery system 60 generally comprises an aerosol generating device 13 configured to generate a continuous aerosol stream, a pressurizing device 62 configured to provide a gas stream separate from the continuous aerosol stream, a mixing reservoir 66 configured to combine the continuous aerosol stream and the gas stream to form a mixture, one or more conduits 43 (e.g. cannulas, face masks, or endotracheal tubes) for delivering the mixture as a third stream to the patient, and a regulatory device 64 which varies the flow rate of the gas stream with a frequency of patient expiration. The aerosol may be, for example, nebulized droplets, spray droplets (both of which can be dried after forming), or a dry powder. Accordingly, the aerosol generating device 13 may be, for example, a nebulizer, an aerosol sprayer (e.g. metered dose inhaler (MDI) or softmist generator (e.g. Respimat)), or a dry powder inhaler (DPI). In some exemplary embodiments, the pressurizing device 62 and regulatory device 64 may be integral and provided as a single device 63. A conduit 43 may include the one or more ports 45 which ultimately emit the third stream being delivered to the patient. Synchronization of reductions in the flow rate with patient expiration provides periodic temporary retention of the mixture in the mixing reservoir and intermittency to the delivery of the third stream to the patient.

In some exemplary embodiments, the mixing reservoir 66 may be provided by a heater-mixer 10, 30, 40, or 50 as previously discussed and illustrated in FIGS. 1A-1D. This may advantageously combine the advantages of reduction of aerosol droplet size and improved efficiency of aerosol drug delivery. For instance, a mixing reservoir 66 and a pressurizing device 62 may provided by a mixer-heater 40 or 50, where the mixing region 11 serves as mixing reservoir 66. The external pressurized gas source 28 (connected to compressed air inlets 26 in FIG. 1C) or, alternatively, the fans 41 (in FIG. 1D) serve as the pressurizing device 62. In these instances, regulatory device 64 may control the flow of compressed air to inlets 26 or the fan speed of fans 41.

The aerosol generating device 13 may be configured to generate the continuous aerosol stream at a constant rate. Alternatively, the rate may be varied, although a rate greater than zero output is preferably maintained.

As identified in the Background section, another source of high aerosol drug losses, particularly during mechanical ventilation, is deposition in the aerosol delivery system conduits, including but not limited to the aerosol source adapter, connectors, cannulas, face masks and endotracheal tubes. As used herein, "conduit" may be any tube or tubule used or usable for conducting a stream, such as of an aerosol or gas, in an aerosol delivery system.

Figure 5A:
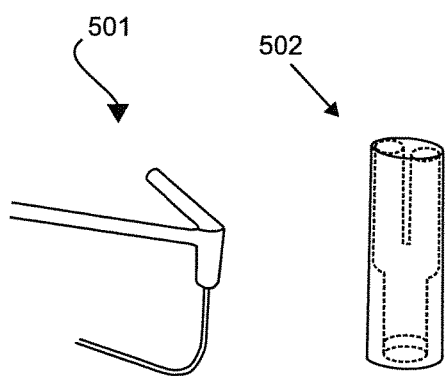
FIGS. 5A-5D are conventional conduit components which have sharp changes in flow direction or sudden contractions/expansions in conduit diameter.
Figure 5B:
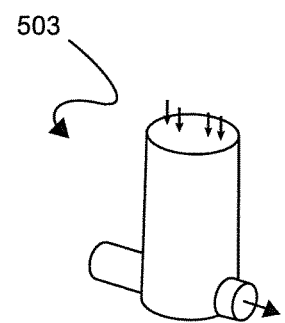
Figure 5C:
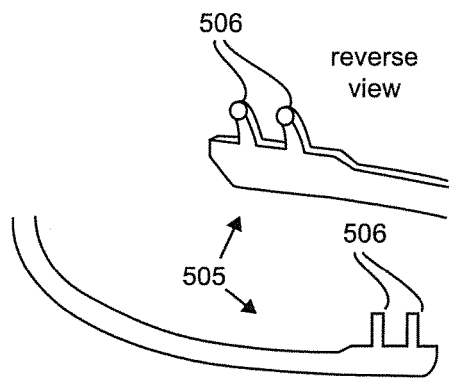
Figure 5D:
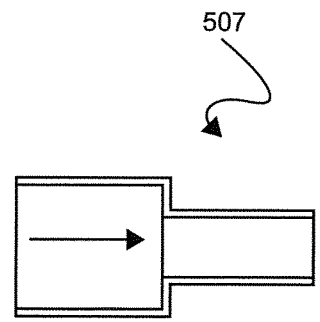

FIGS. 5A-5D show some conduits where high depositional losses commonly occur. FIG. 5A shows two traditional Y-connectors (i.e. wye-connector) 501 and 502, FIG. 5B a traditional aerosol inlet adapter (T-connector) 503, FIG. 5C a traditional nasal cannula 505 with aerosol delivery ports 506, and FIG. 5D an adapter or tube 507 with a change in conduit diameter. A nasal cannula 505 such as that shown in FIG. 5C may be used for noninvasive ventilation. The three dimensional geometries of these conduit elements generally give one or more of significant changes in flow direction or cross-sectional size (e.g. conduit diameter).

FIGS. 6A-6C show what may be referred to herein as exemplary "streamlined" conduits. The streamlined passageways and devices may advantageously reduce flow disruption and turbulence. As a result, pressure drops through the connectors may be decreased, gas mixing and gas dispersion may be reduced, and pharmaceutical aerosol loss in the ventilation circuit may be minimized. Conduits which may be "streamlined" include but are not limited to connectors in mechanical ventilation tubing, aerosol inlet adapters (T-connectors), Y-connectors, adaptors for administering pharmaceutical aerosols, metered dose inhaler (MDI) spacers, in-line dry powder inhaler (DPI) devices, aerosol holding chambers, submicrometer and nanometer aerosol generators, aerosol mixer-heaters, and respiratory inhalers including DPI, MDI, nebulizer, and softmist style devices. FIG. 6A shows two exemplary streamlined Y-connectors 601 and 602, FIG. 6B a streamlined aerosol inlet adapter 603, FIG. 6C a streamlined nasal cannula 605 with aerosol delivery ports 606, and FIG. 6D an adaptor or tube 607 with a change in conduit diameter. As apparent from a comparison of FIGS. 5A-5D and FIGS. 6A-6D, exemplary streamlined conduits have smooth transitions in flow direction and cross-sectional size and shape. The three dimensional geometries of these components eliminate sharp changes in flow direction and sudden expansions and contractions of the cross-sectional area.

A metric by which streamlining may be described and assessed is the centerline radius of curvature (RC) divided by the largest diameter in the vicinity of the feature (which may be, for example, an inlet or outlet diameter). The resulting geometric ratio of centerline radius of curvature to diameter (i.e. RC/D) can be applied to changes in flow direction as well as changes in conduit diameter.

Figure 7A:
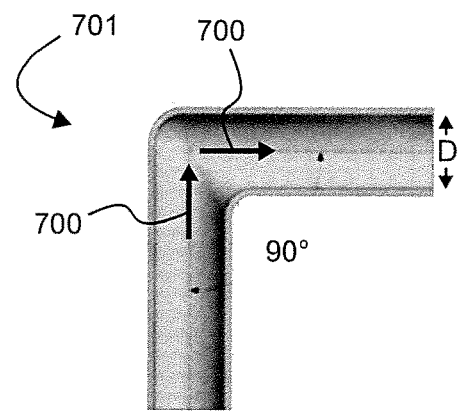
FIGS. 7A-7C are conduit portions evaluated according to a streamlining metric.
Figure 7B:
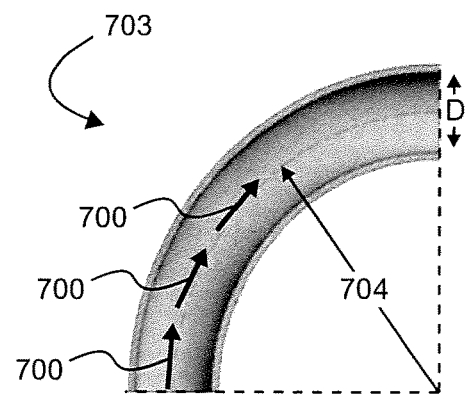
Figure 7C:
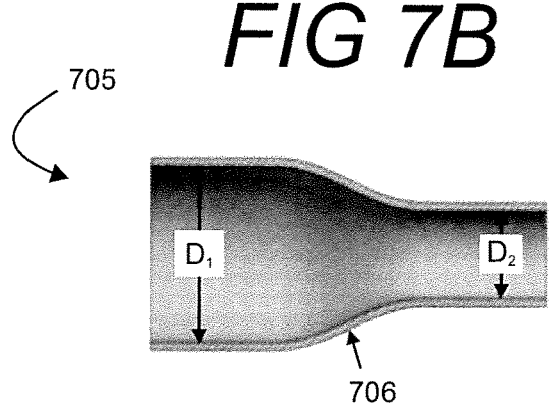

FIGS. 7A-7C show three example conduit elements or features assessed according to the RC/D ratio. In exemplary embodiments, conduits which change a flow direction of a conducted stream have a geometric ratio (RC/D) of at least 0.5. This metric gives substantial reductions in aerosol depositional losses, as exemplified in the Examples section below. A geometric ratio (RC/D) of at least 0.6, 0.7, 0.8, or 0.9 would also be acceptable. In exemplary systems with a need for still lower depositional losses, conduits which change a flow direction of a conducted stream may have a geometric ratio (RC/D) of at least 1.0. "Flow direction" as used herein refers to the primary net direction of movement of an aerosol or gas through a conduit or other conducting structure. For most conduits and in particular those with a circular or elliptical cross section, flow direction at a point in the conduit is generally collinear with a center longitudinal axis of the conduit. If the center longitudinal axis is curved, flow direction is collinear with a tangent line taken at a point along the curve. In FIGS. 7A-7C, flow direction at a few selected points are identified by arrows 700. For purposes of this invention, any change from one point to a subsequent point along a flow path of greater than 5 degrees may be described as a change in flow direction. As can be seen by the three arrows in FIG. 7C, there is a change in flow direction between each of the arrows.

In exemplary embodiments, conduits which have a change in conduit diameter have sigmoidally curved walls (i.e. the walls have a shape of a sigmoidal curve) where the change in diameter occurs, and the sigmoidally curved walls have a geometric ratio (RC/D) of at least 0.5. A geometric ratio (RC/D) of at least 0.6, 0.7, 0.8, or 0.9 would also be acceptable. For an even greater reduction in depositional losses, exemplary embodiments may have conduit portions with a geometric ratio (RC/D) of at least 1.0 at locations where a change in diameter occurs. These geometric ratio values may be applied to a wide range of conduit types, including but not limited to Y-connectors, T-connectors, and nasal cannulas (e.g. for noninvasive ventilation).

In FIG. 7A, conduit 701 has a sharp 90° bend in flow direction, as is characteristic in current mechanical ventilation systems. This gives a 0° radius of curvature at the centerline, so RC=0.0. Thus, irrespective of the diameter (D), the conduit 701 has geometric ratio (RC/D) 0.0. Conduit 701 is not streamlined and would be expected to exhibit high depositional losses when conducting an aerosol stream. In the example of FIG. 7B, the conduit 703 has a centerline radius of curvature (RC) 704 of 15 mm. The diameter (D) is 5 mm. Thus, the geometric ratio (RC/D)=3.0 and satisfies even the least stringent streamlining requirement (i.e. that RC/D be at least 0.5). In the example of FIG. 7C, the conduit 705 has a change in flow passage diameter. Notably, the walls providing the change in diameter are sigmoidal curves 706. In this case, the centerline radius of curvature (RC) is 20 mm. The diameter of interest is the largest of the diameters in the vicinity of the change. Thus, given that diameter D1 is larger than diameter D2, D1 should be used in the determination of RC/D. In this example, D1 is 20 mm. Hence the geometric ratio (RC/D) is 1.0, again satisfying the streamlining requirement. Table 1 provides a listing of further examples of conduits which were developed with the streamlining feature.

TABLE 1

Approximate values of centerline radius of curvature divided by conduit diameter for all streamlined designs.

| Device | Feature | Minimum RC of Feature (mm)$^a$ | Largest Diameter of Feature (mm) | RC/D |
|---|---|---|---|---|
| Adult single inlet cannula with 5 × 7.5 mm nasal prongs | Change in direction | 10 | 8 | 1.25 |
| Adult double inlet cannula with 5 × 7.5 mm nasal prongs | Change in flow direction | 8 | 8 | 1.0 |
| Low flow streamlined cannula | Change in flow direction | 8.5 | 4 | 2.1 |
| Infant Y-connector | Change in direction | 10 | 10 | 1.0 |
|  | Change in diameter | 23 | 10 | 2.3 |
| Adult Y-connector | Change in direction | 20 | 20 | 1.0 |
|  | Change in diameter | 45 | 20 | 2.25 |
| Infant T | Change in diameter | 18 | 24 | 0.75 |
| Adult T | Change in diameter | 40 | 53 | 0.75 |

$^a$For devices with multiple features, the reported feature produces the minimum RC/D.

Figure 8:
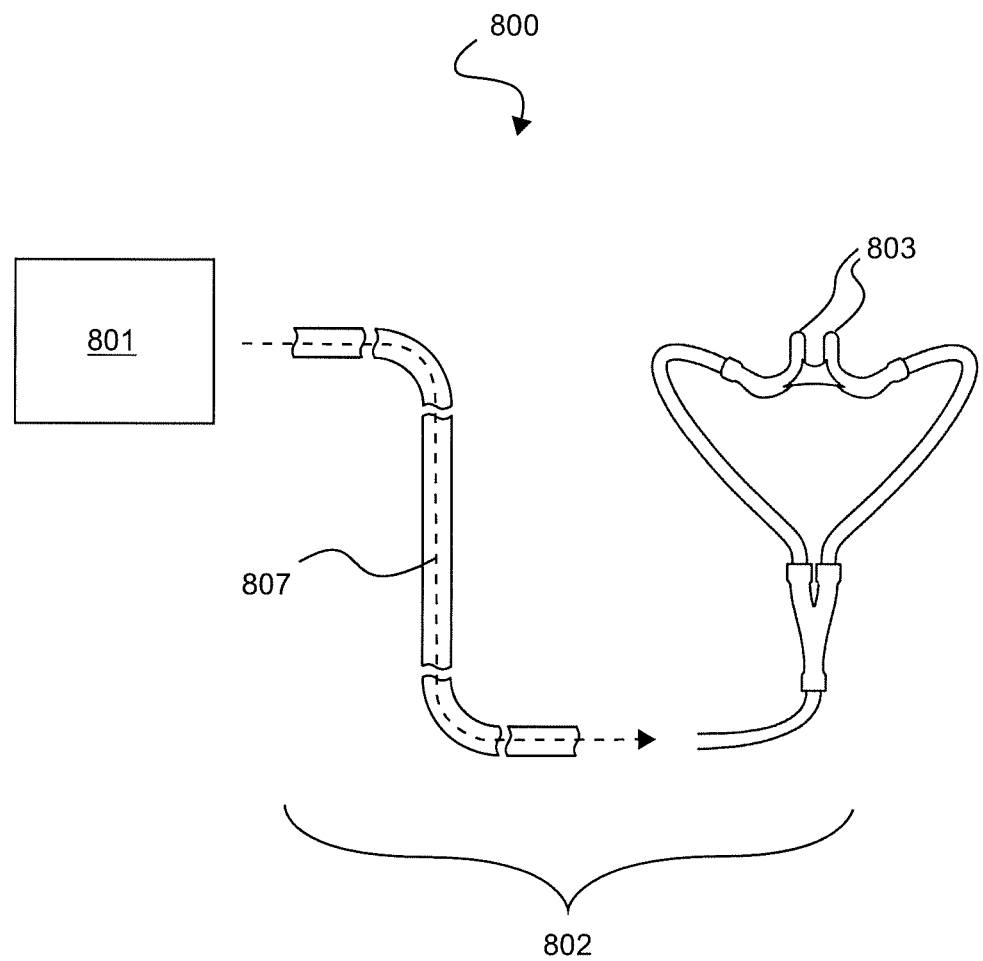
FIG. 8 is a schematic for a system with streamlined components.

FIG. 8 schematically shows an exemplary system 800 for delivering one or more aerosols to a patient. At the start of the system 800, a flow output device 801 generates a stream of the one or more aerosols. The flow output device may be or include, for example, a ventilator and/or an aerosol generating device such as a nebulizer. Alternative aerosol delivery devices include sprayers (e.g. metered dose inhaler (MDI) or softmist inhaler) and dry powder inhalers (DPI). The end of the system may be identified by one or more ports 803 configured to deliver the stream to the patient. If the system is noninvasive, the one or more ports 803 may be, for example, one or two openings of a nasal cannula. Alternatively, if the system is invasive, the one or more ports 803 may be, for example, an endotracheal tube. One or more conduits 802 are arranged to conduct the aerosol stream by completing a path 807 between the flow output device 801 and the one or more ports 803. Generally, such a path 807 may not be entirely linear, with the effect that the one or more conduits 802 change a flow direction of the stream at least once along the path 807. It is advantageous that all portions of the one or more conduits 802 which change a flow direction of the stream along the path 807 have a geometric ratio of centerline radius of curvature to diameter (RC/D) of at least 0.5, or more preferably, at least 1.0. In the case that the system 800 has one or more conduits 802 which include at least one change in conduit diameter, it is furthermore advantageous for all portions of the one or more conduits 802 which have a change in conduit diameter have sigmoidally curved walls where the change occurs, and the sigmoidally curved walls have a geometric ratio of centerline radius of curvature to diameter (RC/D) that is likewise at least 0.5, or more preferably, at least 1.0.

For noninvasive systems according to FIG. 8, the one or more conduits 802 may include one or more nasal cannulas which terminate in the one or more ports 803. In some exemplary embodiments, the system 800 is configured to emit the aerosol stream at the one or more ports 803 with a flow rate of 10-60 liters per minute (LPM). Alternatively, the system 800 may be configured to emit the aerosol stream at the one or more ports 803 with a flow rate of 2-20 LPM. As yet another alternative, the system 800 may be configured to deliver the aerosol stream at the one or more ports 803 with a flow rate of 1-5 LPM. The airflow rate determines the level of respiratory support provided to the patient and is often selected based on clinical status. The lower flow rates will be employed for children, infants and neonates.

Figure 9:
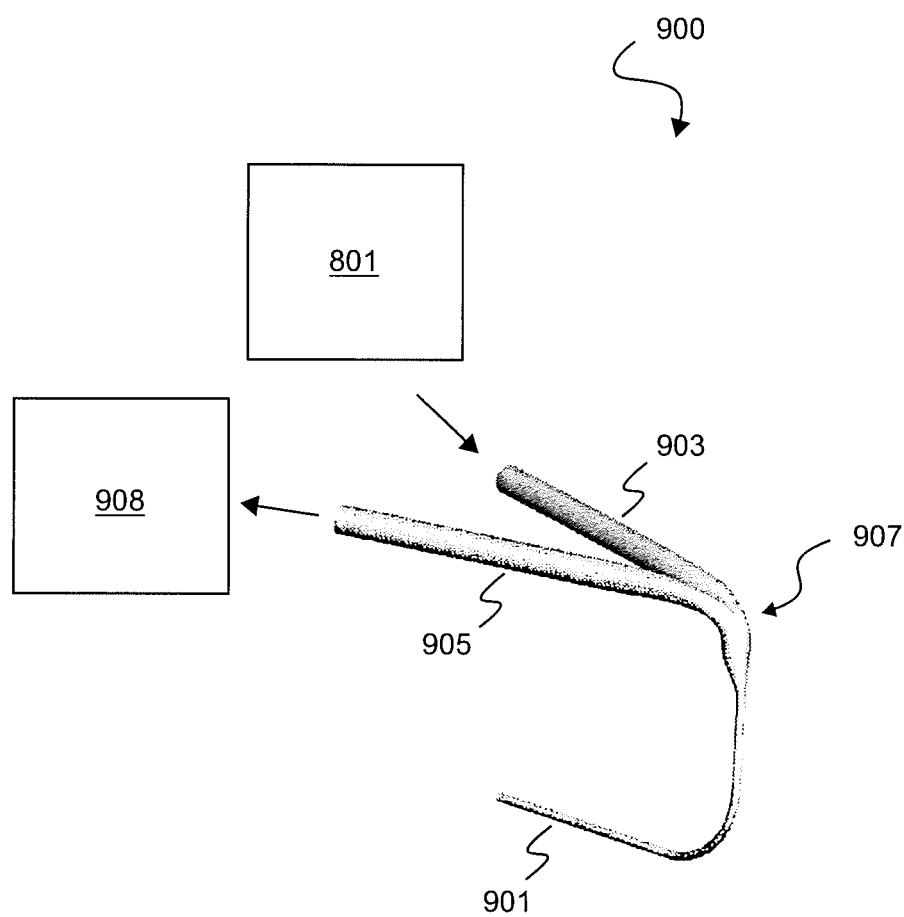
FIG. 9 is a diagram for an invasive ventilation system using a streamlined Y-connector.

In addition to reduced aerosol depositional losses, some exemplary systems with streamlined conduit features as discussed above also have the advantage of a reduction in rebreathed $CO_2$ during invasive ventilation. Generally, a system 800 such as that which is depicted in FIG. 8 may be used for delivering one or more gases and/or one or more aerosols. System 800 of FIG. 8 is not limited to aerosol delivery. FIG. 9 shows a schematic of an exemplary system 900 which includes additional details pertinent to invasive ventilation of a patient using, for example, an endotracheal tube 901. An inspiratory line 903 conducts a stream which may contain oxygen among other possible constituents. This is directed from flow output device 801 toward the endotracheal tube 901 inserted into the patient. An expiratory line 905 is separately provided for conducting deoxygenated air (generally with high $CO_2$ content) from the patient away from the endotracheal tube 901. The inspiratory line 903 and expiratory line 905 may be joined at a connector such as Y-connector 907, which serves to split a single conduit from the endotracheal tube into the inspiratory and expiratory lines 903 and 905. The expiratory line 905 may be connected to a device 908 for generating a flow in the expiratory line 905 away from the endotracheal tube 901. In some systems, the flow output device 801 for the inspiratory line 903 and the device 908 for the expiratory line 905 may be integrally connected as part of one control device such as a ventilator. Here, the inspiratory line 903, expiratory line 905, and Y-connector 907 are all conduits corresponding to conduits 802 in the more generalized system 800 of FIG. 8. In exemplary systems, each of these conduit components, especially the Y-connector 907, have a geometric ratio (RC/D) of at least 0.5, or more preferably, at least 1.0, wherever changes in flow directions and/or changes in conduit diameter occur.

For a streamlined aerosol or gas delivery system 800 of FIG. 8, it is particularly advantageous that no fewer than all components which conduct an aerosol and which have either or both a change in flow direction and a change in conduit diameter meet the geometric ratio RC/D requirements set forth herein. While streamlining of a first component is itself desirable to reduce depositional losses at that first component, a downstream second component which does not meet streamlining requirements may still result in considerable deposition, thereby reducing the overall effectiveness of streamlining within the system 800.

FIG. 10 shows a method 1000 for delivering one or more gases and/or one or more aerosols to a patient. Method 1000 corresponds with system 800 of FIG. 8. At step 1001, a stream of either or both an aerosol and gas is generated, e.g. with a flow output device. At step 1003, the stream is conducted through one or more conduits along a path between the flow output device and one or more ports delivering the stream to the patient. At step 1005, a flow direction of the stream is changed at least once along the path, where all changes in flow direction are made with one or more portions of the one or more conduits which have a geometric ratio of centerline radius of curvature to diameter of at least 0.5. More preferably, this ratio may be at least 1.0. It should be noted that the steps of method 1000 would in general occur simultaneously.

Example 1

The goal of this study was to evaluate in vitro the efficiency of an "intermittent aerosol delivery mode" using condensational growth methods during non-invasive ventilation by simulating three different physiological breathing profiles through an adult nose-mouth-throat (NMT) model. Intermittent administration was considered by delivering aerosol during either the entire inhalation time or half of the inhalation time, when the inspiratory flow was higher than the average flow rate.

In this example, we describe the use of a mixer-heater with compressed air inlets according to what is shown and described in connection with FIGS. 1A, 1B, and 1C. Operation in an intermittent delivery mode was found to be superior, with respect to maximizing the dose delivered to the lungs and minimizing exhalation losses, compared to the continuous mode.

In Vitro Nasal Delivery Setup

The components of the aerosol delivery system were the aerosol mixer-heater with compressed air inlets (see FIG. 1C) used to generate submicrometer aerosol by mixing a stream of heated recycled air, the ventilator tubing (70 cm length and 10 mm internal diameter, Instrumentation Industries Inc., Bethel Park, Pa.) to transport the aerosol to the cannula. Two different nasal cannulas were employed: an EEG streamlined single inlet, and a divided ECG cannula, with separate inlets for a) the mixture stream (containing mixed aerosol stream and heated gas stream) and b) heated and humidified high flow air. The cannula was positioned at the nostrils of the NMT model, which was connected to a low resistance filter (PulmoGuard II, Quest Medical, Brockton, Mass.) and the breathing simulator (ASL 5000, Ingmar Medical, Pittsburgh). The characteristics of the realistic breathing profiles are given in Table 2. The NMT model was placed in an environmental chamber (Espec, Hudsonville, Mich.) under conditions of 37±0.5° C. and RH>90%.

Aerosols were generated from the Aeroneb Lab nebulizer (Aerogen Limited, Ireland) using a formulation containing 0.2% albuterol sulfate and 0.2% sodium chloride in deionized water. Compressed air for the gas streams was supplied to the mixer-heater according to the side channel inlet configuration shown and described for FIGS. 1B and 1C.

The compressed air was supplied at 20 L/min using two protocols: (i) 2 sec on and 2 sec off, (ii) 1 sec on and 3 sec off. This may be achieved using a three-way solenoid valve (ASCO, Florham Park, N.J.) controlled by a timer and was synchronized such that the air was delivered during the 2 second inhalation. FIG. 11 shows the timing of the intermittent delivery in combination with breathing profile 1. In the ECG protocol, an additional 15 L/min supersaturated air (43° C., RH>90%) was delivered through the second inlet of the nasal cannula patient interface. Control experiments were performed by continuously delivering the air through the mixer-heater.

TABLE 2

Simulated breathing profiles measured at the nostrils of the nose-mouth-throat model

| Breathing Profiles | Peak Inspiratory Flow (L/min) | Inhaled Volume, $V_t$ (L) | Breathing Frequency, f (Breaths/min) | Average Inhalation Flow (L/min)* |
|---|---|---|---|---|
| 1 | 23 | 0.50 | 15 | 15 |
| 2 | 35 | 0.75 | 15 | 22.5 |
| 3 | 44 | 0.93 | 15 | 27.9 |

*$2 \times V_t \times f$

Emitted Dose and In Vitro Deposition Measurement and Analysis

In order to quantify the dose delivered to the nasal delivery components during a period of 1 min aerosolization, a PulmoGuard II filter was positioned at the outlet of the mixer-heater, with the rest of the in vitro components (i.e. ventilator tubing, cannula, and NMT model) downstream of this filter. The mass of drug collected on this filter using breathing profile 1 was determined as the mixer-heater emitted dose.

In vitro aerosol delivery device deposition and delivery through the NMT model was determined using the following method. Aerosol was generated into the mixer-heater which was equilibrated to heat the incoming air to 37° C. to produce a submicrometer aerosol. Aerosol was delivered from the mixer-heater using the intermittent delivery mode, which was synchronized with the respiration cycle for a total of 1 minute. Synchronization was such that delivery of the mixed stream (formed from the mixed aerosol stream and heated gas stream) to the patient was synchronized with inhalation. During exhalation, the aerosol stream continued to be admitted to the mixer-heater, but the heated gas stream flow was cut off. As a result, aerosol droplets were permitted to accumulate in the mixing region of the mixer-heater but were not immediately passed out of the system and delivered to the patient. The nasal delivery setup components (i.e. 70 cm tubing, nasal cannula, NMT model, and the PulmoGuard filter) were detached and rinsed using known volumes of deionized water. The mass of albuterol sulfate on each component was determined using a validated high performance liquid chromatography analytical method (3). Each experiment was repeated 3-4 times. One-way ANOVA followed by Tukey's HSD post hoc test were performed to compare continuous delivery with the two intermittent delivery modes. Two-way ANOVA, followed by two-tailed student t-test and Tukey's HSD were used to study the effect of timing mode (1-second vs 2-second) and breathing pattern (profiles 1-3), respectively. All statistical tests were performed using JMP® Pro 10.0.2, (Cary, N.C.), with a p-value of <0.05 as the indicator of significance.

Results

Emitted Dose

The mean (standard deviation) albuterol sulfate dose emitted from the mixer-heater during continuous delivery was 82.4 (2.2) % of the nominal dose. The nominal dose was determined based on the weight difference of the nebulizer before and after the nebulization and the measured albuterol sulfate concentration of the formulation. The mean emitted doses during 2- and 1-second intermittent deliveries were 73.61 (2.45) and 76.26 (5.94) %, respectively. Delivery from the mixer-heater was greater than 70% of the nominal dose, despite utilization of the intermittent delivery mode.

Tables 3 and 4 reveal low drug deposition in the delivery setup and the in vitro model of the nose, mouth and throat indicating that the submicrometer aerosol was efficiently delivered from the mixer-heater and through the NMT model to the lungs using the ECG delivery method. Similar low drug deposition was observed for EEG delivery as shown in tables 5 and 6.

TABLE 3

Mean (standard deviation) deposition as a percentage of the emitted dose in each device component during continuous and intermittent enhanced condensation growth delivery modes and simulation of three breathing profiles

| Component | Breathing Profile 1 | | | Breathing Profile 2 | | Breathing Profile 3 | |
|---|---|---|---|---|---|---|---|
| | Continuous | 2 sec | 1 sec | 2 sec | 1 sec | 2 sec | 1 sec |
| Nebulizer | 0.92 (0.37) | 0.53 (0.13) | 0.88 (0.24) | 1.06 (0.57) | 0.88 (0.33) | 0.86 (0.40) | 0.44 (0.13) |
| Tubing | 3.21 (0.64) | 4.57 (0.59) | 5.47 (0.71) | 3.09 (0.99) | 5.88 (0.96) | 3.5 (1.23) | 4.26 (1.22) |
| Cannula | 1.36 (0.45) | 0.99 (0.29) | 4.13 (1.45) | 1.32 (0.33) | 3.85 (1.44) | 1.14 (0.12) | 2.61 (0.95) |

TABLE 4

Mean (standard deviation) deposition as a percentage of the emitted dose in the NMT during different enhanced condensation growth delivery modes

| Breathing Profile | Continuous | 2 sec | 1 sec |
|---|---|---|---|
| Profile 1 | 2.70 (0.25) | 2.65 (0.33) | 5.86 (0.86) |
| Profile 2 | N/A | 2.99 (0.39) | 6.61 (1.40) |
| Profile 3 | N/A | 4.45 (1.61) | 6.16 (2.61) |

TABLE 5

Mean (standard deviation) deposition as a percentage of the emitted dose in each device component during excipient enhanced growth with continuous and intermittent delivery modes and simulation of three breathing profiles

| Component | Breathing Profile 1 | | | Breathing Profile 2 | | Breathing Profile 3 | |
|---|---|---|---|---|---|---|---|
| | Continuous | 2 sec | 1 sec | 2 sec | 1 sec | 2 sec | 1 sec |
| Nebulizer | 0.56 (0.4) | 0.73 (0.38) | 1.07 (1.29) | 1.22 (0.36) | 1.55 (2.17) | 0.58 (0.20) | 0.60 (0.21) |
| Tubing | 2.60 (0.19) | 4.43 (1.25) | 4.76 (0.92) | 6.21 (0.86) | 5.09 (1.28) | 5.35 (2.06) | 6.15 (1.82) |
| Cannula | 0.23 (0.11) | 0.60 (0.33) | 0.48 (0.48) | 0.57 (0.24) | 1.18 (0.8) | 0.45 (0.42) | 0.82 (0.55) |

TABLE 6

Mean (standard deviation) deposition as a percentage of the emitted dose in the NMT during excipient enhanced growth with continuous and intermittent delivery modes

| Breathing Profile | Continuous | 2 sec | 1 sec |
|---|---|---|---|
| Profile 1 | 0.31 (0.22) | 0.88 (0.23) | 0.60 (0.40) |
| Profile 2 | N/A | 1.20 (0.20) | 2.10 (1.10) |
| Profile 3 | N/A | 1.45 (0.22) | 3.87 (0.55) |

Lung delivery increased when an intermittent delivery of either 1 or 2 seconds was employed. Also, increasing the tidal volume of the inhalation profiles also increased amount of drug delivered to the lung. Increased lung deposition corresponded with a decrease in the respiratory losses when the intermittent delivery mode was employed compared to continuous delivery. Lung dose and respiratory losses obtained using the EEG delivery mode show a similar trend of increased pulmonary dose and lower respiratory losses for the intermittent mode versus the continuous delivery from the mixer-heater. For EEG mode, during continuous delivery using profile 1, the mean lung delivery and respiratory losses were 31.6% and 64.7%, respectively. Similar values far 1 second delivery during EEG were 62.5% and 30.6%. Increasing the tidal volume using profile 3 increased the mean lung delivery to 74.4% and decreased the respiratory losses to 14.1%.

Example 2

In this example, a heater-mixer comprising fans as shown and described in connection with FIG. 1D was used. As was the case for Example 1, the interior of the heater-mixer was arranged according to the combination of FIGS. 1A and 1B. In both Examples 1 and 2, the countercurrent heat exchanger was implemented containing metal walls separating the side flow passages from the inner heating channel. Resistive film heaters (Kapton®; DuPont Kapton® #KHLV-202/10, Circleville, Ohio, USA) were attached to the metal walls to heat both the incoming gas in the side channels prior to mixing with the aerosol and the aerosol mixture in the central channel. The two fans generate the gas stream flow which mixes with the aerosol stream inside the mixer-heater and controls the flow of the mixed (third) stream for actual delivery of the aerosol droplets to the patient.

In this example, the blower system comprised a power supply, function generator, and two fans (i.e. blowers). An Accel TS200-1B Modulated Power Supply (Irvine, Calif., USA) was used to amplify a Sine waveform. It is capable of producing a signal with peaks at −20 V and 20 V with a gain of +10 V/V, and the signal may be shifted by using an offset. The waveform was generated with an Agilent 15 MHz Function/Arbitrary Waveform Generator (Santa Clara, Calif., USA), which is able to produce both sine and square wave functions. The two blowers used were Dynatron 12 V DC Blowers (Fremont, Calif., USA), which are each capable of producing air flow up to 198 L/min in a resistance-free system.

Figure 12:
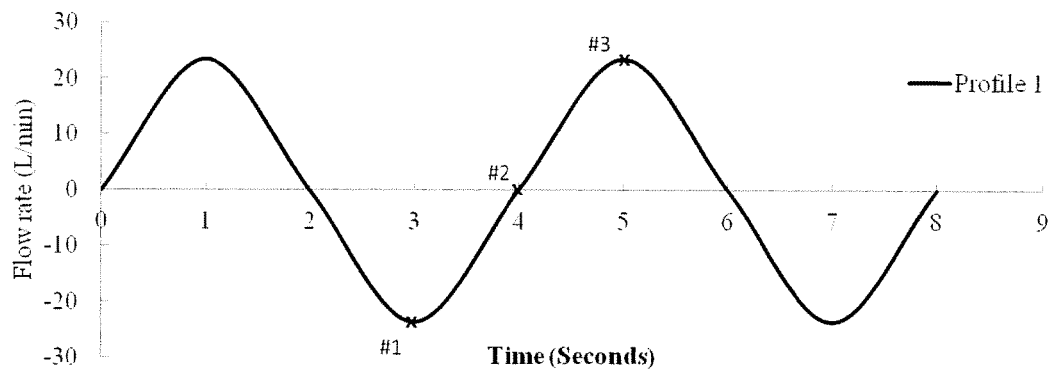
FIG. 12 shows fan/blower activation points during breathing profile 1.

In tests for optimization, the effect of activating the blowers at three points in the simulated breathing cycle, marked as points 1-3 in FIG. 12, were investigated. The drug (albuterol sulfate) doses emitted from the mixer-heater with fans in EEG mode were measured and are given in Table 7. By comparing the emitted dose data in Table 7 it was shown that the dose emitted from mixer-heater with fans did not vary with changing the activation point of the blowers with respect to breathing profile 1. The dose emitted from the mixer-heater with fans was consistently above 90% of the nominal dose in all cases using profile 1. However, point 1 was the point in time that the activation of the fans resulted in generating an overlapping flow profile similar to the breathing profile 1. It was also found that 600 mVPP was the required voltage to get a peak flow of 23 L/min, which was also the peak flow rate of breathing profile 1 (see Table 2). In light of these understandings we chose point 1 and 600 mVPP as the activation point of the fans in our continuing experiments to avoid unwanted drug losses resulting from the mismatch of the waveform generated by the mixer-heater with fans and the breathing profile 1.

TABLE 7

Effect of blower activation during the breathing cycle on the emitted dose of the mixer-heater at 600 mV using breathing profile 1 with a peak inhalation flow of 23 L/min

| Activation Point | Emitted Dose (% Nominal Dose) |
|---|---|
| 1 | 91.0 (2.1) |
| 2 | 92.0 (0.6) |
| 3 | 93.1 (2.6) |

The emitted dose from the mixer-heater with fans using breathing profiles 2 and 3 (Table 2), were also measured in EEG and ECG modes. The emitted dose was found on average lower with breathing profiles 2 (76.92%) and 3 (70.69%) compared to breathing profile 1 (91.62%) during EEG delivery. Emitted dose was lower using ECG delivery mode compared to EEG with the three breathing profiles (62.98, 57.7, and 57.6% for profiles 1-3, respectively). Based on our observations a portion of exhalation flow and in the case of ECG the constant air flow delivered to the second nostril may flow back to the mixer-heater with fans through the ventilator tubing. This appears significant at the higher breathing flow rates with profiles 2 and 3 compared to profile 1. This back flow changes the resistance of the delivery line, which in turn may affect the performance of the blowers and reduce the emitted dose. A change in the performance of the fans was observed in the ECG case, where in order to have a flow profile at the outlet of the mixer-heater with fans similar to EEG the input voltage of the fans had to be increased to 900 mVPP in ECG instead of 600 mVPP in EEG delivery.

Despite the apparent breathing flow rate dependence of the emitted dose from the mixer-heater with fans, the respiration losses in EEG were found comparable to the mixer-heater with compressed air inlets using the three breathing profiles 1-3. The mean respiratory losses using profiles 1, 2 and 3 were 31.1, 17.2 and 16.3%, respectively for the mixer-heater with fans. Similar values for the mixer-heater with compressed air inlets were 30.6, 17.0 and 14.1%, respectively during EEG with 1 second intermittent delivery. The lung doses with the mixer-heater with fans were independent of the breathing pattern employed. The mean lung delivery using profiles 1, 2, and 3 were 42.7, 40.8 and 34.1%, respectively. However they were lower than those observed with the mixer-heater with compressed air inlets due to higher ventilator tubing and cannula and nose losses. The mean device and nose deposition using the mixer-heater with fans were 15.9 and 4.5%, for profile 1, 16.6 and 6.2% for profile 2 and 17.0 and 8.0% for profile 3. Similar values for the mixer-heater with compressed air inlets were 4.8 and 0.5%, 6.0 and 1.6%, and 5.7 and 2.4%, respectively. Tubing, cannula and nose losses increased with increasing breathing pattern flow rate.

The lung doses were also measured in ECG mode. The lung doses increased with breathing profiles 2 and 3 (48.0% and 44.9%, respectively, compared to 30.8% for profile 1), suggesting that using ECG mode, a higher inspiratory flow rate would increase lung deposition. It should be noted that with mixer-heater with fans in ECG mode the lung doses were lower than with mixer-heater with compressed air inlets for profiles 1-3. The mean lung doses for profiles 1, 2 and 3 using the mixer-heater with compressed air inlets were 52.1, 59.1 and 72.0%, respectively using 1 sec intermittent flow, compared to similar values of 30.8, 48.0 and 44.9%, respectively for the mixer-heater with fans. Using the mixer-heater with fans the lung doses with profiles 1-3 in ECG were lower than EEG, for example, 30.8% vs 42.7% using profile 1 for ECG vs EEG.

Example 3: Reduction of $CO_2$ Re-Breathing Using Streamlined Components During Invasive Mechanical Ventilation The re-breathing of expired $CO_2$ gas may limit the effectiveness of mechanical ventilation. At $CO_2$ inhalation levels near 3%, moderate respiratory stimulation to hypercapnia occurs. Elevated inhaled $CO_2$ levels are of particular concern for ventilated infants, where the tidal volume to dead space ratio is much smaller than in adults.

Figures 13A, 13B, 13C:
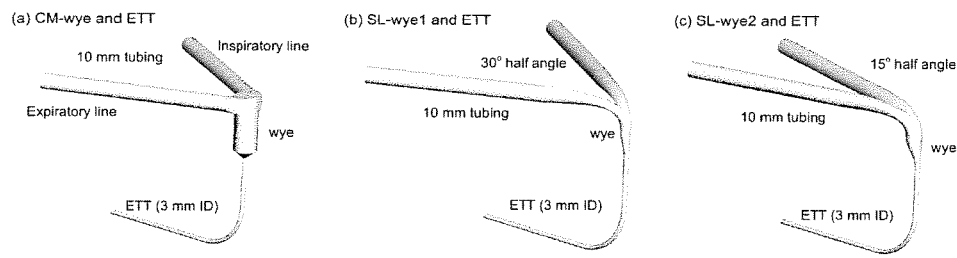
FIG. 13 shows invasive mechanical ventilation circuits for an infant, including inspiratory and expiratory lines, wye connectors, and an endotracheal tube (ETT). Wye connectors evaluated were (A) commercial (CM), (B) streamlined (SL) with a 30° half angle of each line (wye1) and (C) streamlined (SL) with a 15° half angle of each line (wye2)
Figures 15A, 15B, 15C, 15D:
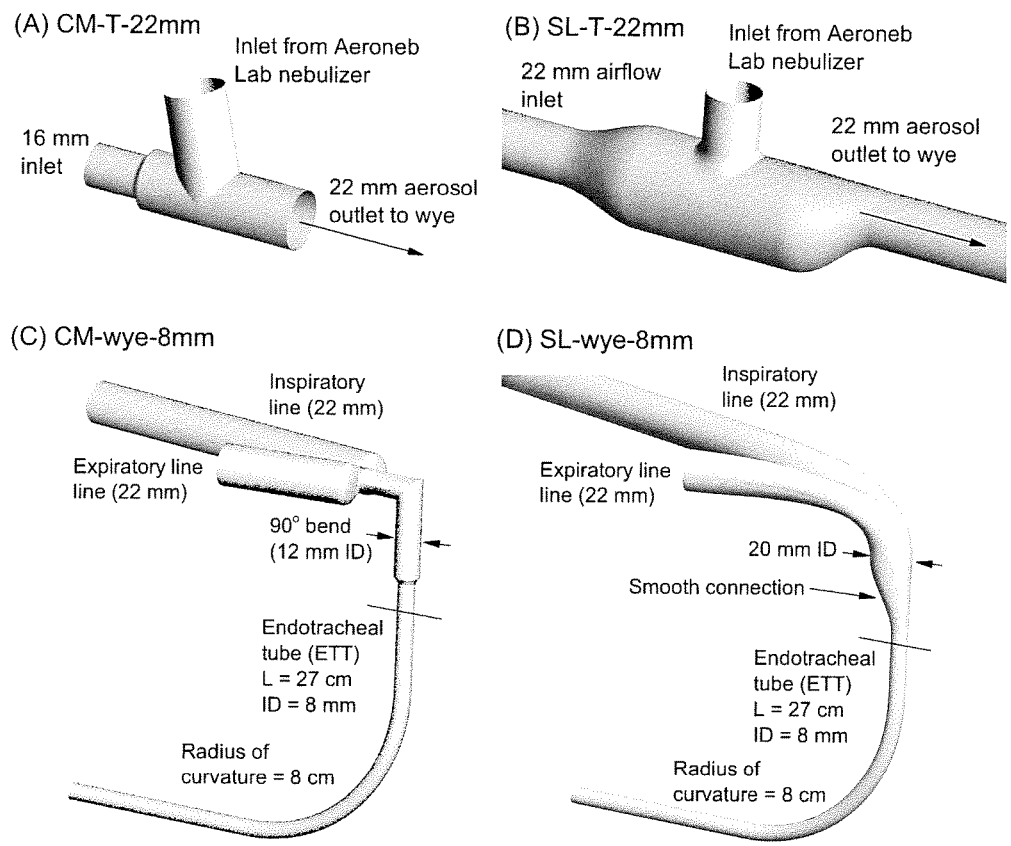
FIG. 15 shows commercial and streamlined components for invasive gas and aerosol delivery to an adult including the (A) commercial and (B) streamlined T-connectors for ventilation tubing as well as (C) commercial and (D) streamlined wye-connectors coupled to an ETT.

The objective of this example was to evaluate the average $CO_2$ concentration entering the lungs of an infant during invasive mechanical ventilation using commercial vs. streamlined circuit components. The ventilation circuits considered are illustrated in FIGS. 13A-13C. Each circuit contains 10 cm lengths of inspiratory and expiratory ventilator tubing with a diameter of 1 cm. The inspiratory and expiratory lines are joined at the wye connector, which leads to an endotracheal tube (ETT) with an ID of 3 mm.

A commercial (CM) wye geometry was selected to represent current practice (FIG. 13A). Streamlined designs were developed that eliminated sharp expansions and contractions and sudden changes in flow direction by applying a centerline radius of curvature greater than 5 mm. All streamlined components met the requirement that the geometric ratio RC/D was at least 0.5 for changes in flow direction and changes in conduit diameter. The two streamlined designs have half angles between the inspiratory and expiratory lines of either 30° (SL-wye1; FIG. 13B) or 15° (SL-wye2; FIG. 13C).

Computational fluid dynamics (CFD) simulations were used to model the flow field and transport of respiratory gases.

Mass fractions (%) of $CO_2$ at the peak of inspiratory flow during the 2nd inhalation cycle were measured and compared. With the CM-wye design, elevated concentrations of $CO_2$ are observed to enter the ETT. This is because of mixing in the wye region of the inspiratory air with the gas in the expiratory line, which pulls high levels of exhaled $CO_2$ into the inspired airstream.

Both streamlined designs largely reduce these $CO_2$ values in the ETT and entering the lungs. The streamlined designs demonstrate reduced mixing of the inspired gas with the high concentration $CO_2$ in the expiratory line. Values of time-averaged $CO_2$ mass fraction entering the lungs over the entire inhalation pulse for the CM-wye, SL-wye1, and SL-wye2 designs are 2.2%, 1.1%, and 1.5%, respectively. As a result, the commercial design provides $CO_2$ values that are near the expected moderate hypercapnia response level of 3%. In contrast, the SL wye designs reduce the average inspired concentration of $CO_2$ by a factor of 1.5-2.0 fold.

Example 4: Reduced Pressure Drop During Inhalation

The streamlined wye connector may reduce pressure drop through the mechanical ventilation circuit making it easier for the patient to take an unassisted breath (spontaneously breathe). To determine the reduction in pressure drop associated with the streamlined designs, CFD simulations were performed for the infant wye circuits shown in FIGS. 13A-13C. Circuit components and flow rates were consistent with a newborn infant. The pressure drop which was presented to the patient during inhalation is significantly lower in the streamlined models. Pressure drop through the circuits is quantified based on inlet pressure to drive a flow rate of 5 LPM. The associated inlet pressures for the CM-wye, SL-wye1, and SL-wye2 designs were 672.2 Pa, 360.5 Pa, and 370.2 Pa, respectively. Therefore, the streamlined components reduce the required effort to generate a spontaneous breath characterized by a tracheal flow rate of 5 LPM by a factor of 2 fold.

Example 5: Reduced Pressure Waveform Peaks

The streamlined designs may reduce the maximum and minimum pressures required to generate a prescribed flow waveform. In this example, the infant commercial and streamlined wye geometries were again considered with transient inhalation consistent with a newborn infant. As before, CFD simulations were used to model the transient flow field accounting for the effects of turbulent flow.

Inspiratory and expiratory peak pressure and flow values for the infant waveform are reported in Table 8 based on the CFD simulations. As indicated, the flow waveform was held constant in all cases. For both inspiratory and expiratory flow, the streamlined geometries reduced the peak system pressures by a factor of approximately 2 fold. Moreover, the CM-wye2 design had the lowest peak inspiratory pressure of all designs considered. Based on this reduction in peak pressures, the streamlined designs may cause less pressure trauma to the airways. Alternatively, for pressure-controlled ventilation, the streamlined wye connectors may provide elevated gas flow delivery at a specified maximum pressure.

TABLE 8

Pressure waveform peak values (inspiratory and expiratory) as a function of wye design for a prescribed infant inhalation waveform

| Wye Design | Peak inspiratory flow rate (LPM) | Peak inspiratory pressure (Pa) | Peak expiratory flow rate (LPM) | Peak expiratory pressure (Pa) |
|---|---|---|---|---|
| CM-wye | 7.8 | 1629.1 | 1.95 | −150.6 |
| SL-wye1 | 7.8 | 856.8 | 1.95 | −72.2 |
| SL-wye2 | 7.8 | 835.0 | 1.95 | −74.1 |

Example 6: Improved Aerosol Drug Delivery During Non-Invasive Ventilation in Adults Aerosol drug delivery efficiency during noninvasive ventilation (NIV) according to conventional techniques is known to be low (~10%) and is associated with poor outcomes of aerosol therapy. The objective of this example was to demonstrate the benefit of redesigning ventilation circuit components using a streamlining approach to improve aerosol delivery during nasal high flow therapy (HFT) in adults with a conventional-sized aerosol from a mesh nebulizer. The non-invasive ventilation circuit consisted of a humidifier, mesh nebulizer, mixing T-connector (with 90° angle), 10 mm tubing, and nasal cannula interface. In vitro experiments were used to evaluate depositional losses in a system of existing components and a newly proposed streamlined T-connector and cannula at a flow rate of 30 LPM.

The commercially available T-connector for coupling the Aeroneb series of mesh nebulizers with 10 mm tubing is the neonate design. The neonate T-connector is illustrated in FIG. 14A and features a 22 mm top inlet to accommodate the Aeroneb mesh nebulizer (Aerogen Limited, Galway, Ireland), a 9 mm air inlet, and a 10 mm air outlet. Length of the air outlet available for particle deposition in the T-connector may depend on the insertion depth of the tube and in this study was 5 mm. The component naming convention in this study is based on the device design—tubing size—and type of component. The name Base-10-T indicates a commercial (base) design, compatibility with 10 mm tubing, and a T-connector component.

To redesign the Base-10-T component for efficient aerosol drug delivery at flow rates consistent with high nasal cannula flow therapy, a streamlined design was developed, as illustrated in FIG. 14B. The streamlined T-connector allows for insertion of the Aeroneb mesh nebulizer as with the commercial unit. Preliminary CFD simulations were used in order to minimize deposition within the streamlined T-connector. Based on these simulations, it was determined that an exemplary final design should maintain velocity within the mixing region below 2 m/s and should eliminate recirculation along the top of the T-connector downstream of the nebulizer. The final streamlined design uses gradual size change from the inlet 10 mm tubing through a larger 24 mm internal diameter and back through the 10 mm outlet. The sigmoidal curves at the inlet and outlet of the streamlined T-connector have radii of curvatures of approximately 18 and 22 mm, respectively. The larger diameter of the T-connector allows more room for the aerosol to change direction without striking a surface. The outlet tube of the streamlined T-connector may be in-line with the top of the main flow passage, which minimizes recirculation in this important region. A smoothed connection is used to join the Aeroneb branch with the main flow passage. Implementation of this smoothed connection may reduce turbulence generation sites, flow detachment, and recirculation. Finally, a perforated plate may be used to unify the inlet flow and produce a more unidirectional stream through the entrainment region below the nebulizer. Unifying the flow refers to reducing velocity gradients and regions of recirculation that can enhance particle deposition. The result is the streamlined (SL) and perforated (p) design, denoted SLp-10-T, which has a total length of 12 cm. As an alternative, a tin design was used to unify the inlet flow. Circular fins were implemented along with a filled central region with the intent of eliminating a central jet moving through the entrainment region and resulting in the SLf-10-T design.

For the nasal cannulas, 10 mm tubing was again selected along with conventional large bore nostril prongs. The Optiflow (Fisher and Paykel, Irvine, Calif.) nasal cannula was selected as the base case. In the current study, the medium-sized adult Optiflow cannula was evaluated with a 10 mm inlet line and approximate outlet prong diameter of 5 mm (Base-10-CL; FIG. 14C). The connective tubing was 20 cm in length with an internal diameter of 10 mm. To create a more realistic delivery scenario compared with straight tubing, a gradual 90° bend of the tube was employed, as illustrated in the figure. The cannula outlets form an approximately 60° angle with a horizontal plane. To navigate the delivery circuit, the aerosol must traverse a 90° bend in the T-connector, a 90° bend in the connective tubing, turn 90° to enter the cannula prongs, and finally turn an additional 60° to enter the nose. This has the result of 330° in aerosol direction change.

The exemplary streamlined cannula design shown has a single 10 mm inlet and smoothed elliptical flow passage for the aerosol to enter the left or right nostril (FIG. 14D). Preliminary CFD simulations were used to understand the flow field and minimize flow features that contributed to deposition. The division point of the two nostril prongs was selected at a position that evenly divided the flow between the left and right nostrils. This exemplary streamlined cannula also includes nasal prongs containing oval outlets with major and minor diameters of 7.5 and 5 mm, respectively. The oval shape may reduce recirculating velocity in the cannula and exit velocities at the nose. In this exemplary embodiment, the flow passages have centerline radii of curvatures in the range of 10-13 mm with a distance of 14 mm between the nasal prongs centers. The streamlined cannula (SL-10-CL) has a diameter reduction from the 10 mm inlet tubing to 8 mm in the main cannula passage, which is part of a quick-connect design. In the present example, conventional aerosols are considered with a two pronged streamlined design.

Different combinations of the base and streamlined components were assembled to determine deposition within individual components and total drug throughput, i.e., emitted dose, for a composite NIV system. Considering the application of nasal high flow therapy in adults, typical flow rates of 30 and 45 LPM through the system were evaluated using CFD. Reducing the flow rate below 30 LPM will improve aerosol throughput but may also diminish oxygen delivery during HFT and potentially reduce lung function. Individual cases considered in this study are described in Table 9. Briefly, Case 1 combines the commercial T-connector and cannula elements, Cases 2 and 3 consider the streamlined components, and Case 4 tests performance of the Optiflow cannula with a streamlined T-connector. These four cases were evaluated at 30 LPM in the in vitro experiments.

In vitro experimental studies were used to evaluate the initial size of the aerosol exiting the Aeroneb Lab nebulizer in the absence of the NIV setups and to determine aerosol deposition in each component of the delivery system as well as total throughput, or emitted dose, for Cases 1-4 at 30 LPM. In all experiments, the drug formulation was aqueous-based with 0.2% w/v albuterol sulfate (AS) in deionized water. The Aeroneb Lab nebulizer was operated for 30 s resulting in an average nominal dose of approximately 463 µg of drug (with the average value range of 447-494 µg for the four cases studied). Drug deposition in the individual components of each delivery case was evaluated using a validated HPLC-UV method for AS.

Experimentally determined deposition fractions (DF) and emitted dose (ED) as a percentage of nominal dose, as well as standard deviations (SD), are presented in Table 10 for Cases 1-4. Deposition fractions in the nebulizer are low for all cases, which represents the drug mass deposited in the nebulizer unit downstream of the vibrating mesh. Considering the T-connectors, the highest deposition is observed in the Base-10-T design (30.6%), which is reduced to approximately 5% with the streamlined options. Deposition fractions in the cannula increase as emission increases through the streamlined T-connectors. Case 4 illustrates increased cannula DF for the Base-10-CL when the SL-wye geometry is implemented. To determine the effect of the SL cannula independent of the T-connector design employed, deposition efficiency (DE) should be considered. The cannula DE is calculated as the ratio of the aerosol mass depositing in the cannula divided by the aerosol mass entering the cannula. Cannula DEs for the commercial (Case 1) and streamlined (Case 2) designs calculated from DF values are 35.6 and 29.4%, respectively. As a result, the streamlined cannula design may reduce drug loss by a factor of 1.2. Considering overall emitted dose (ED) (Table 10), the streamlined designs (Cases 2-4) provide a large improvement to the commercial product (Case 1).

Streamlined geometries offer an effective method to significantly improve the delivery of aerosols through components of NIV systems. This increase in drug delivery efficiency is important for new inhaled medications with narrow therapeutic windows, increased costs, or long delivery times.

TABLE 9

Combinations of commercial (base) and streamlined (SL)
T-connectors, tubing, and cannulas to form NIV cases.

| | Flow rate (LPM) | T-connector | Tubing | Cannula |
|---|---|---|---|---|
| Case 1 | 30 and 45 | Base-10-T | 20 cm of 10 mm tubing | Base-10-CL |
| Case 2 | 30 and 45 | SLp-10-T | 20 cm of 10 mm tubing | SL-10-CL |
| Case 3 | 30 and 45 | SLf-10-T | 20 cm of 10 mm tubing | SL-10-CL |
| Case 4 | 30 and 45 | SLp-10-T | 20 cm of 10 mm tubing | Base-10-CL |

Abbreviations:
10, 10 mm tubing;
Base, commercially available base case unit;
CL, cannula;
f, fin design;
p, perforated plate design;
SL, streamlined;
T, T-connector

TABLE 10

Experimental results of deposition fractions (DF) as a percentage of nominal dose
presented as mean (SD) values for a steady flow rate of 30 LPM.

| | Nebulizer DF (%) | T-Connector DF (%) | 20 cm of tubing DF (%) | Cannula DF (%) | Total device $DF^a$ (%) | Emitted Dose (%) |
|---|---|---|---|---|---|---|
| Case 1 | 7.1 $(5.4)^b$ | 30.6 (1.9) | 19.0 (0.6) | 15.4 (3.0) | 72.1 (6.2) | 27.8 (6.1) |
| Case 2 | 4.9 (2.0) | 5.7 (0.4) | 27.2 (2.2) | 18.3 (1.1) | 56.1 (2.6) | 44.0 (2.6) |
| Case 3 | 6.4 (1.1) | 5.1 (2.4) | 32.8 (4.0) | 16.8 (1.6) | 61.1 (4.4) | 38.9 (4.4) |
| Case 4 | 5.1 (2.0) | 5.1 (1.3) | 30.3 (9.0) | 26.2 (2.6) | 66.7 (7.4) | 33.3 (7.4) |

$^a$Sum of component DF values.
$^b$SD based on n = 4 experiments.

Example 7: Improved Aerosol Delivery During Mechanical Ventilation with an Endotracheal Tube Patients receiving invasive mechanical ventilation with an endotracheal tube (ETT) can often benefit from pharmaceutical aerosols; however, drug delivery through the ventilation circuit according to conventional methods is known to be very inefficient. The objective of this example was to improve the delivery of aerosol through an invasive mechanical ventilation system for an adult by redesigning circuit components using a streamlining approach. Redesigned components were the T-connector interface between the nebulizer and ventilator line and the wye connector leading to the ETT.

Aerosols were generated using two commercial vibrating mesh nebulizers. The two mesh nebulizers considered were the Aeroneb Lab (Aerogen Limited, Galway, Ireland) and the Eflow Rapid (Pari Respiratory Equipment, Midlothian, Va.).

The commercial and streamlined T- and wye-connectors are illustrated in FIGS. 15A-15D. The streamlined components were constructed to minimize flow disruption by avoiding sudden expansions and contractions in the flow stream and eliminating sharp changes in flow direction. Instead, sigmoidal curves are used for changes in flow pathway diameter and radii of curvatures are applied to smooth changes in flow direction. The final exemplary streamlined designs shown in FIGS. 15A-15D are the result of an iterative process that implements CFD to minimize aerosol deposition and drug loss. Components are denoted as commercial (CM) or streamlined (SL), followed by the geometry type (T- or wye connector), and the outlet size. For example, CM-wye-8 mm represents the commercial wye geometry with an outlet for connecting to an 8 mm internal diameter ETT.

For the T-connector, an expanded region of aerosol mixing may be implemented to accommodate momentum from the aerosol stream and thereby reduce impaction on the lower wall below the nebulizer. Streamlined connections may be used to interface the 22 mm ventilator tubing with the expanded mixing region. The overall design of the streamlined T-connector may be similar to the previously proposed 10 mm tubing design proposed in Example 7 for a noninvasive ventilation nasal cannula system. The outlet of the T-connector may be positioned in the upper portion of the mixing region, which was found to minimize recirculation and deposition.

The streamlined wye connector removes a number of sudden expansions and contractions that the aerosol must navigate in the commercial system. A radius of curvature is added to the 90° bend region of the wye to minimize flow disruption and aerosol impaction. Identical ETTs are implemented for comparison of the commercial and streamlined designs. It is noted that an exemplary streamlined wye connector does not increase the volume of the ventilator circuit. The streamlined T-connector may increase the volume of the inspiratory line. However, this is not a concern because only air from the ventilator (and not expired gas) is expected to be in the inspiratory tubing.

In vitro experiments were used to determine the initial size distribution and deposition of the aerosol produced by the two nebulizers (i.e. Aeroneb Lab and Eflow Rapid). In all experiments, the drug formulation was aqueous-based with 0.2% w/v albuterol sulfate (AS) in deionized water.

The MMAD (and GSD) values for the Lab and Eflow nebulizers were 4.84 μm (5.7) and 5.30 μm (1.6), respectively.

Deposition fraction (DF) of drug in the individual system components is presented in Table 11 based on in vitro experiments for the commercial system. These values are presented as a percentage of dose emitted from the nebulizer at an airflow rate of 30 LPM. Deposition fractions in the Aeroneb Lab and Eflow nebulizers were approximately 3-5% and 18-28% of nominal dose, respectively (not shown in Table 11). Based on these large differences in nebulizer deposition fraction, values reported in Table 11 were based on the dose delivered from the nebulizer. Deposition in the Aeroneb T-connector is relatively low (<10%) for the applied steady state conditions (Table 11). The Eflow device was connected directly in-line with the wye inlet and a T-connector was not present. High deposition in the wye (33-39%) and ETT (9-36%) resulted in overall device deposition of 58-72%. The filter deposition fraction ($DF_{filter}$) represents emitted dose (ED) at the ETT outlet. The emitted dose was observed to increase with increasing ETT diameter.

Deposition fraction results for the streamlined components at 30 LPM based on in vitro experiments are presented in Table 12. These experimental results are again based on the emitted dose from the nebulizer. The streamlined T-connector is observed to significantly reduce deposition by a factor of 2-3× (t-test, p=0.019, p=0.0001, and p<0.0001 for 7, 8, and 9 mm ETT, respectively). However, deposition in the T-connector is low for both the commercial and streamlined models. The largest improvement with the streamlined designs was observed for the wye connector, where deposition is reduced by a factor of approximately 4-9× (t-test, p<0.0001 for all SL-wyes vs. their respective CM-wyes for Aeroneb and How studies). As a result of reducing deposition in the streamlined wye geometries, a larger aerosol enters the ETT, which increases deposition in this region. The smallest ETT is observed to have the largest increase in depositional losses.

Emitted dose (ED), which is equal to the filter deposition fraction ($DF_{filter}$), is compared between the two systems as an $ED_{ratio}$, calculated as $$ED_{ratio} = \frac{\text{Streamlined } DF_{filter}}{\text{Commercial } DF_{filter}}$$

The improvements in ED associated with streamlining range from 1.1 to 1.5 with higher $ED_{ratio}$ values associated with larger ETTs (Table 12).

In summary, the experimental results demonstrated that the streamlined components improved delivery through the circuit by factors ranging from 1.3-1.5 compared with a commercial system for adult ETT sizes of 8 and 9 mm. Streamlined components may significantly improve the delivery of pharmaceutical aerosols during mechanical ventilation using multiple aerosol generation devices, ETT sizes, and flow rates.

TABLE 11

Mean (SD) deposition fraction (DF) as a percentage of dose emitted from the nebulizer at a flow rate of 30 LPM for the commercial components based on in vitro experiments.

| Components | T-connector | Wye | ETT | Device | Filter |
|---|---|---|---|---|---|
| Aeroneb Lab | | | | | |
| CM-Wye-7 mm | 7.8 (2.3) | 36.4 (2.3) | 24.9 (2.5) | 69.2 (2.7) | 30.8 (2.7) |
| CM-Wye-8 mm | 7.1 (1.8) | 39.9 (2.4) | 16.6 (1.6) | 63.6 (1.5) | 36.4 (1.5) |
| CM-Wye-9 mm | 9.1 (1.3) | 39.0 (2.6) | 9.4 (2.6) | 57.6 (4.3) | 42.4 (4.3) |
| Eflow | | | | | |
| CM-Wye-7 mm | | 37.0 (5.8) | 35.5 (6.6) | 72.4 (0.8) | 27.6 (0.8) |
| CM-Wye-8 mm | | 32.6 (3.2) | 31.0 (2.3) | 63.6 (4.9) | 36.4 (4.9) |
| CM-Wye-9 mm | | 33.9 (4.6) | 26.7 (9.0) | 60.6 (4.6) | 39.4 (4.6) |

TABLE 12

Mean (SD) deposition fraction (DF) as a percentage of dose emitted from the nebulizer at a flow rate of 30 LPM for the streamlined components based on in vitro experiments and emitted dose (ED) ratio.

| Components | T-connector | Wye | ETT | Device | Filter | $ED_{ratio}$[a] |
|---|---|---|---|---|---|---|
| Aeroneb Lab | | | | | | |
| SL-Wye-7 mm | 4.8 (0.6) | 5.6 (0.8) | 55.9 (1.6) | 66.3 (2.0) | 33.7 (2.0) | 1.1 |
| SL-Wye-8 mm | 3.1 (0.6) | 5.4 (1.3) | 40.1 (8.5) | 48.6 (9.9) | 51.4 (9.9) | 1.4 |
| SL-Wye-9 mm | 2.0 (1.2) | 4.3 (1.2) | 31.6 (4.7) | 37.9 (6.7) | 62.1 (6.7) | 1.5 |
| Eflow | | | | | | |
| SL-Wye-7 mm | | 6.5 (2.1) | 58.5 (3.4) | 65.0 (2.5) | 35.0 (2.5) | 1.3 |
| SL-Wye-8 mm | | 8.6 (1.0) | 43.9 (4.7) | 52.4 (5.3) | 47.6 (5.1) | 1.3 |
| SL-Wye-9 mm | | 5.2 (1.6) | 37.2 (9.2) | 42.4 (8.1) | 57.6 (8.1) | 1.5 |

[a] Emitted dose ratio ($ED_{ratio}$) calculated as (Streamlined $DF_{filter}$)/(Commercial $DF_{filter}$)

While exemplary embodiments of the present invention have been disclosed herein, one skilled in the art will recognize that various changes and modifications may be made without departing from the scope of the invention as defined by the following claims.

Having thus described our invention, what we claim as new and desire to secure by Letters Patent is:

1. A method of administering an aerosol to a patient, comprising steps of:
   generating a continuous aerosol stream comprising an aerosol larger than 2 µm with a nebulizer;
   providing a gas stream separate from said continuous aerosol stream with a pressurizing device;
   combining said continuous aerosol stream and said gas stream in a mixing reservoir to form a mixture;
   heating said mixture such that said aerosol is reduced to sizes smaller than 2 µm;
   delivering said mixture as a third stream to said patient; and
   varying a flow rate of said gas stream with a frequency of patient respiration, wherein synchronization of reductions in said flow rate with patient expiration provides periodic temporary retention of said mixture in said mixing reservoir and intermittency to said delivering of said third stream.

2. The method of claim 1, wherein said continuous aerosol stream is constant.

3. The method of claim 1, wherein said frequency is in the range of 12 to 50 cycles per minute.

4. The method of claim 1, wherein said frequency is 6 to 7.5 cycles per minute.

5. A system for administering an aerosol to a patient, comprising:
   an aerosol generating device which generates a continuous aerosol stream comprising an aerosol larger than 2 µm;
   a pressurizing device which provides a gas stream separate from said continuous aerosol stream;
   a mixer-heater device comprising
     a mixing reservoir configured to combine said continuous aerosol stream and said gas stream to form a mixture, and
     a channel portion connected to said mixing reservoir, wherein said channel portion is configured to admit an aerosol larger than 2 µm and to heat said mixture to reduce the aerosol size to smaller than 2 µm;
   one or more conduits for delivering said mixture as a third stream to said patient; and
   a regulatory device which varies a flow rate of said gas stream with a frequency of patient respiration, wherein synchronization of reductions in said flow rate with patient expiration provides periodic temporary retention of said mixture in said mixing reservoir and intermittency to said delivering of said third stream.

6. The system of claim 5, wherein said nebulizer is configured to generate said continuous aerosol stream at a constant rate.

7. The system of claim 5, wherein said frequency is in the range of 12 to 50 cycles per minute.

8. The system of claim 5, wherein said frequency is 6 to 7.5 cycles per minute.

9. The system of claim 5, wherein said aerosol generating device is selected from a group consisting of a nebulizer, a metered dose inhaler (MDI), a softmist inhaler, and a dry powder inhaler (DPI).

10. The system of claim 5,
    wherein said channel portion includes a center channel having at least two opposing planar walls, and
    wherein said center channel is configured to admit aerosol droplets larger than 2 µm and to conduct said third stream in a first direction and said at least two opposing planar walls are configured to heat said third stream within said center channel to 28 to 70° C. to reduce aerosol droplet size to sizes smaller than 2 µm.

11. The system of claim 10, wherein said pressurizing device is one or more fans.

12. A system for delivering an aerosol to a patient, comprising:
    a flow output device which generates an aerosol stream;
    one or more ports configured to deliver said aerosol stream to said patient; and
    all conduits configured to conduct said aerosol stream by completing a path between said flow output device and said one or more ports, said conduits changing a flow direction of said aerosol stream along said path at least once,
    wherein all portions of said conduits which change a flow direction of said aerosol stream along said path have a geometric ratio of centerline radius of curvature to diameter of at least 0.5.

13. The system of claim 12, wherein said geometric ratio is at least 1.0.

14. The system of claim 12, wherein
    said conduits include at least one change in conduit diameter, and
    all portions of said conduits which have a change in conduit diameter have sigmoidally curved walls where said change occurs, said sigmoidally curved walls having a second geometric ratio of centerline radius of curvature to diameter of at least 0.5.

15. The system of claim 14, wherein said second geometric ratio is at least 1.0.

16. The system of claim 12, wherein said conduits include one or more of a Y-connector, a T-connector, and a nasal cannula.

17. The system of claim 16, wherein
    said aerosol stream comprises oxygenated air,
    said conduits include
      an inspiratory line which conducts said aerosol stream comprising oxygenated air from said flow output device toward an endotracheal tube inserted into said patient,
      an expiratory line which conducts deoxygenated air from said patient away from said endotracheal tube, and
      a Y-connector configured to split a single conduit from said endotracheal tube into said inspiratory line and said expiratory line.

18. The system of claim 16, wherein said conduits include one or more nasal cannulas terminating in said one or more ports.

19. The system of claim 18, wherein said system is configured to emit said aerosol stream at said one or more ports with a flow rate of 10 to 60 LPM.

20. The system of claim 18, wherein said system is configured to emit said aerosol stream at said one or more ports with a flow rate of 2 to 20 LPM.

21. The system of claim 18, wherein said system is configured to emit said aerosol stream at said one or more ports with a flow rate of 1 to 5 LPM.

* * * * *